United States Patent
Trang et al.

(10) Patent No.: US 11,298,569 B2
(45) Date of Patent: Apr. 12, 2022

(54) METHODS AND COMPOSITIONS FOR MODULATING OPIOID WITHDRAWAL SYMPTOMS

(71) Applicant: UTI Limited Partnership, Calgary (CA)

(72) Inventors: Tuan Trang, Calgary (CA); Nicole Burma, Calgary (CA)

(73) Assignee: UTI Limited Partnership, Calgary (CA)

( * ) Notice: Subject to any disclaimer, the term of this patent is extended or adjusted under 35 U.S.C. 154(b) by 0 days.

(21) Appl. No.: 16/308,955

(22) PCT Filed: Jun. 13, 2017

(86) PCT No.: PCT/CA2017/050728
§ 371 (c)(1),
(2) Date: Dec. 11, 2018

(87) PCT Pub. No.: WO2017/214725
PCT Pub. Date: Dec. 21, 2017

(65) Prior Publication Data
US 2019/0351008 A1 Nov. 21, 2019

Related U.S. Application Data

(60) Provisional application No. 62/349,327, filed on Jun. 13, 2016.

(51) Int. Cl.
| | | |
|---|---|---|
| *A61P 25/36* | (2006.01) | |
| *A61K 9/00* | (2006.01) | |
| *A61K 9/06* | (2006.01) | |
| *A61K 9/70* | (2006.01) | |
| *A61K 31/195* | (2006.01) | |
| *A61K 31/473* | (2006.01) | |
| *A61K 38/08* | (2019.01) | |

(52) U.S. Cl.
CPC ............ *A61P 25/36* (2018.01); *A61K 9/0014* (2013.01); *A61K 9/0019* (2013.01); *A61K 9/0053* (2013.01); *A61K 9/06* (2013.01); *A61K 9/7023* (2013.01); *A61K 31/195* (2013.01); *A61K 31/473* (2013.01); *A61K 38/08* (2013.01)

(58) Field of Classification Search
None
See application file for complete search history.

(56) References Cited

U.S. PATENT DOCUMENTS

| | | | |
|---|---|---|---|
| 2006/0128708 A1* | 6/2006 | Diamond | A61K 31/53 514/243 |
| 2012/0135960 A2* | 5/2012 | Mouthon | A61P 43/00 514/64 |
| 2012/0220607 A1* | 8/2012 | Johnson | A61P 3/10 514/262.1 |

FOREIGN PATENT DOCUMENTS

| | | | |
|---|---|---|---|
| WO | 2008116135 A2 | 9/2008 | |
| WO | 2008156758 A1 | 12/2008 | |
| WO | 2009114097 A2 | 9/2009 | |
| WO | 2012019991 A1 | 2/2012 | |
| WO | 2013179264 A2 | 12/2013 | |

OTHER PUBLICATIONS

Navis et al., https://dx.doi.org/10.1021/acschemneuro.0c00333; published Jul. 8, 2020 (Year: 2020).*
Marc A. Schuckit, N Engl J Med 375;4 nejm.org Jul. 28, 2016 (Year: 2016).*
Kosten and George, Sci Pract Perspect. Jul. 2002;1(1):13-20. doi: 10.1151/spp021113 (Year: 2002).*
Rehni et al., CNS & Neurological Disorders—Drug Targets, 2013, vol. 12, No. 1 (Year: 2013).*
Extended Search Report of the European Patent Office dated Jan. 8, 2020 in EP Application No. 17812357.6; 14pgs.
Gödecke et al., "Thrombin-Induced ATP Release From Human Umbilical Vein Endothelial Cells," Am J Physiol Cell Physiol., 302(6):C915-C923, Mar. 2012.
Molica et al., "Functional Role of a Polymorphism in the Pannexin1 Gene in Collagen-Induced Platelet Aggregation," Thromb Haemost., 114(2):325-336, Aug. 2015.
Singh et al. "In Vivo and In Vitro Attenuation of Naloxone-Precipitated Experimental Opioid Withdrawal Syndrome by Insulin and Selective KATP Channel Modulator," Psychopharmacol., 232(2):465-475, 2015.
Burma et al., "Blocking Microglial Pannexin-1 Channels Alleviates Morphine Withdrawal in Rodents," Nat Med., 23 (3):355-360, Mar. 2017.
Gramsch et al., "Changes in Striatal Dopamine Metabolism During Precipitated Morphine Withdrawal," Eur J Pharmacol., 44(3):231-240, Aug. 1977.

(Continued)

*Primary Examiner* — Christina M Borgeest
(74) *Attorney, Agent, or Firm* — Haukaas Fortius PLLC; Michael H. Haukaas

(57) ABSTRACT

A method of screening a compound or a composition for use in modulating opioid withdrawal symptoms in a mammal. The method comprises the steps of: selecting a group of test animals; separating the group into two subgroups; inducing Panx1 activation or expression in both subgroups; dosing a first subgroup with a candidate compound; dosing a second subgroup with a placebo; measuring ATP released in spinal microglia of test animals in the first subgroup and in the spinal microglia of test animals in the second subgroup; quantifying the difference in ATP released in spinal microglia of test animals in the first subgroup and in the spinal microglia of test animals in the second subgroup; if the difference in the ATP released in the first subgroup and the APT released in the second subgroup is greater than 25%, then formulating the candidate compound into a pharmaceutical composition.

11 Claims, 48 Drawing Sheets
Specification includes a Sequence Listing.

(56) References Cited

OTHER PUBLICATIONS

International Search Report and Written Opinion of the ISA/CA dated Jul. 26, 2017 in International Application No. PCT/CA2017/050728; 15pgs.

Moradi et al., "Gap Junction Blockers: A Potential Approach to Attenuate Morphine Withdrawal Symptoms," J Biomed Sci., 20:77, Oct. 2013.

Azizi et al., "Height-Dependent Difference in the Expression of Naloxone-Induced Withdrawal Jumping Behavior in Morphine Dependent Rats," Neurosci Lett., 515(2):174-176, May 2012.

Cándido et al., "Vertical Jumping and Signaled Avoidance," J Exp Anal Behav., 50(2):273-276, Sep. 1988.

Kennes et al., "Changes in Naloxone and Haloperidol Effects During the Development of Captivity-Induced Jumping Stereotypy in Bank Voles," Eur J Pharmacol., 153(1):19-24, Aug. 1988.

Liu et al., "Electrical Stimulation of Nucleus Paragigantocellularis Induces Opioid Withdrawal-Like Behaviors in the Rat," Pharmacol Biochem Behav., 62(2):263-271, Feb. 1999.

Odberg, "The Influence of Cage Size and Environmental Enrichment on the Development of Stereotypies in Bank Voles (Clethrionomys glareolus)," Behav Process., 14(2):155-173, Apr. 1987.

Driessen et al., "Proposal of a Comprehensive Clinical Typology of Alcohol Withdrawal—A Cluster Analysis Approach," Alcohol Alcohol, 40(4):308-313, Jul.-Aug. 2005.

Gamage et al., "Differential Effects of Endocannabinoid Catabolic Inhibitors on Morphine Withdrawal in Mice," Drug Alcohol Depend., 146:7-16, Jan. 2015.

Gamage, "Differential Effects of Endocannabinoid Catabolic Inhibitors on Morphine Withdrawal in Mice," Dissertation—Virginia Commonwealth University., 2008, 229pgs.

Harris et al., "Beta-Adrenergic Antagonists Attenuate Somatic and Aversive Signs of Opiate Withdrawal," Neuropsychopharmacology, 9(4):303-311, Dec. 1993.

Ramesh et al., "Dual Inhibition of Endocannabinoid Catabolic Enzymes Produces Enhanced Antiwithdrawal Effects in Morphine-Dependent Mice," Neuropsychopharmacology, 38(6):1039-1049, May 2013.

* cited by examiner

Fig. 1

SEQUENCE LISTING

<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: 10panx

<400> SEQUENCE: 1

Trp Arg Gln Ala Ala Phe Val Asp Ser Tyr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: scrPanx

<400> SEQUENCE: 2

Phe Ser Val Tyr Trp Ala Gln Ala Asp Arg
1               5                   10

METHODS AND COMPOSITIONS FOR MODULATING OPIOID WITHDRAWAL SYMPTOMS

RELATED APPLICATIONS

This application is a National Stage filing under 35 U.S.C. § 371 of International Application No. PCT/CA2017/050728 filed Jun. 13, 2017, which claims priority under 35 U.S.C. § 119(e) to U.S. Provisional Patent Application No. 62/349,327, filed Jun. 13, 2016, which applications are incorporated herein by reference.

SEQUENCE LISTING

The instant application contains a Sequence Listing that has been submitted electronically in computer readable ASCII format and is hereby incorporated by reference in its entirety. Said ASCII copy, created on Dec. 1, 2020, is named "seq list_ST25" and is 4 kb in size.

TECHNICAL FIELD

The present disclosure generally relates to treatment of substance-use disorders pertaining to an opioid or opioid-like drugs. More particularly, the present disclosure relates to methods for screening compounds and compositions for identification and selection of candidate therapeutic compounds and compositions useful for modulating opioid withdrawal symptoms.

BACKGROUND

Opiates are among the most powerful and widely prescribed drugs for treating pain. However, a major problem in terminating opiate pain therapy is the debilitating withdrawal syndrome that can plague chronic opiate users. The mechanisms involved in opiate withdrawal are poorly understood, and the limited clinical strategies available for treating withdrawal are ineffective.

SUMMARY

The embodiments of the present disclosure generally relate to use of the pannexin-1 (Panx1) channel as a novel therapeutic target for treating morphine withdrawal. We discovered that morphine treatment induces synaptic plasticity in spinal lamina I/II neurons, which manifests as long-term synaptic facilitation upon naloxone-precipitated morphine withdrawal. This synaptic facilitation is critically gated by activation of Panx1 channels expressed on microglia. Pharmacologically blocking Panx1, or genetically ablating this channel specifically from microglia, blocked spinal synaptic facilitation and alleviated the behavioral sequelae of morphine withdrawal. Also tested were clinically utilized non-selective inhibitors of Panx1, mefloquine, and probenecid. These compounds effectively blocked the activation of microglial Panx1, and ameliorated the severity of morphine withdrawal in mice and rats. The findings disclosed herein reveal a novel mechanism by which microglia signal through Panx1 to produce the cellular and behavioral corollary of morphine withdrawal symptoms. Thus, targeting Panx1 represents a potential novel therapeutic approach for treating the symptoms of opiate withdrawal.

BRIEF DESCRIPTION OF THE DRAWINGS

The present disclosure will be described in conjunction with reference to the following drawings in which:

FIG. 1 is a schematic chart depicting a morphine and drug dosing paradigm for studies with rats and mice disclosed herein;

DETAILED DESCRIPTION

Figure 2:
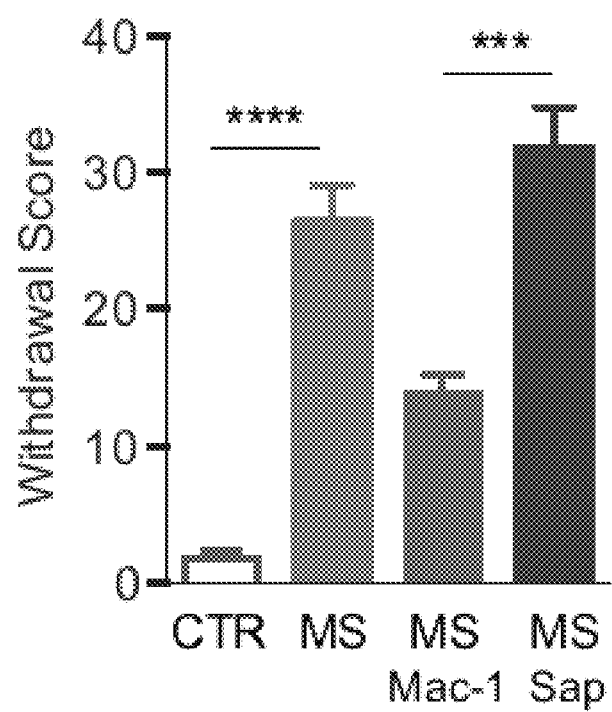
FIG. 2 is a chart showing cumulative withdrawal scores in morphine and control-treated rats and the effects of the immunotoxin Mac-1-saporin on withdrawal behaviours, wherein "CTR" shows control treatments, "MS" show morphine sulfate treatments, "MS Mac-1" shows treatments with intrathecal Mac-saporin, and "MS Sap" shows treatments with intrathecal saporin alone.

The embodiments of the present disclosure relate to methods for screening candidate therapeutic molecules for their potential usefulness for modulation of morphine withdrawal symptoms in mammals.

One embodiment pertains to methods wherein Panx1 is activated in spinal microglia to release ATP as a microglia-to-neuron substrate for unmasking long-term synaptic facilitation in spinal LI/II neurons during naloxone-induced withdrawal. It is disclosed herein that blocking Panx1 effectively alleviates morphine withdrawal without affecting analgesia. The screening methods according to the present disclosure are particularly useful for identifying suitable candidate therapeutic molecules that are able to block Panx1 activation and/or expression.

An example of a method of screening a compound or a composition for use in modulating opioid withdrawal symptoms in a mammal disclosed herein, comprises the steps:
1. selecting a group of test animals;
2. separating the group into two subgroups;
3. inducing Panx1 activation or expression in both subgroups;
4. dosing a first subgroup with a candidate compound;
5. dosing a second subgroup with a placebo;
6. measuring ATP released (i) in the spinal microglia of test animals in the first subgroup, and (ii) in the spinal microglia of test animals in the second subgroup;

7. quantifying the difference in the amount of ATP released (i) in the spinal microglia of test animals in the first subgroup, and (ii) in the spinal microglia of test animals in the second subgroup;
8. if the difference in the amount of ATP released in the first subgroup and the amount of APT released in the second subgroup is greater than 25%, then selecting the candidate compound for incorporation into a pharmaceutical composition.

In one embodiment, the present invention provides a pharmaceutical composition for use in treating opioid withdrawal symptoms in a subject wherein the composition comprises an effective amount of a compound selected through use of the methods disclosed herein, said compound in admixture with a suitable diluent or carrier.

According to another embodiment, the present invention provides a pharmaceutical composition for use in treating opioid withdrawal symptoms in a subject wherein the composition comprises an effective amount of a compound selected to block the subject's pannexin-1 channels. Examples of suitable compounds include the $^{10}$panx peptide, mefloquine, probenecid, and combinations thereof.

Such pharmaceutical compositions can be formulated for intralesional, intravenous, topical, rectal, parenteral, local, inhalant or subcutaneous, intradermal, intramuscular, intrathecal, transperitoneal, oral, and intracerebral use. The composition can be in a liquid, a solid, or a semisolid form, for example pills, tablets, creams, gelatin capsules, capsules, suppositories, soft gelatin capsules, gels, membranes, tubelets, solutions, or suspensions. Alternatively, the composition can be injected intravenously, intraperitoneally, or subcutaneously. Alternatively, the composition may comprise a topical delivery system exemplified by topical creams, lotions, emulsions, and transdermal patches.

The pharmaceutical compositions of the invention can be intended for administration to humans or animals. Dosages to be administered depend on individual needs, on the desired effect, and on the chosen route of administration.

Another embodiment of the present disclosure pertains to use of a candidate compound selected for ameliorating morphine withdrawal symptoms by use of the methods and/or the compounds disclosed herein. Suitable dosing levels are 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, and therebetween. Suitable dosing regimes are 8-h interval applications, twice daily applications, once daily applications, and therebetween. Alternatively, the dosing may be provided over extended periods of time via slow-release transdermal patches Another embodiment of the present disclosure generally relates to compositions comprising one or more compounds selected for blocking a subject's pannexin-1 channels, for example the $^{10}$panx peptide, mefloquine, probenecid, and combinations thereof. Suitable dosing levels are 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, and therebetween. Suitable dosing regimes are 8-h interval applications, twice daily applications, once daily applications, and therebetween.

The pharmaceutical compositions comprising a compound selected through use of the methods disclosed herein, or alternatively, a compound selected to block a subject's pannexin-1 channels, for example the $^{10}$panx peptide, mefloquine, probenecid, and combinations thereof, can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

For example, pharmaceutical compositions of the disclosure comprising a compound selected through use of the methods disclosed herein, or alternatively, a compound selected to block a subject's pannexin-1 channels, for example the $^{10}$panx peptide, mefloquine, probenecid, and combinations thereof, may be formulated for topical administration or alternatively, for transdermal administration to provide dosing over extended periods of time.

A pharmaceutical composition for topical administration may be provided as, for example, ointments, creams, suspensions, lotions, powders, solutions, pastes, gels, hydrogels, sprays, aerosols, dressings, or oils. When formulated in an ointment, the active ingredient may be employed with either a paraffinic or a water-miscible ointment base. Alternatively, the active ingredient may be formulated in a cream with an oil-in-water base or a water-in-oil base. Other formulations the compositions can be incorporated into include oils, suppositories, foams, liniments, aerosols, buccals, and sublingual tablets or topical devices for absorption through the skin or mucous membranes.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays are conveniently delivered from pressurized packs, for example, via a specially shaped closure. Oil-In-Water emulsions can also be utilized in the compositions, patches, bandages and articles. These systems are semisolid emulsions, micro-emulsions, or foam emulsion systems. Usually such a system has a "creamy white" appearance. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes. These can be made with anionic, cationic, nonionic or amphoteric surfactants, or with combinations especially of the nonionic surfactants. A typical invention gel base, provided herein for exemplary purposes only, can contain lecithin, isopropyl palmitate, poloxamer 407, and water. Topical carriers with different viscosities and hand-feel are known to the art. The above active ingredients can be dispersed within the pharmaceutically acceptable carrier in therapeutically effective amounts to treat neuropathies, and the other maladies described above.

A pharmaceutical composition for transdermal administration may be provided as, for example, a hydrogel comprising agents as described herein incorporated into an adhesive patch composition intended to remain in intimate contact with a subject's epidermis for a prolonged period of time. An exemplary adhesive patch composition can comprise a monolithic layer produced by mixing a compound selected through use of the methods disclosed herein, or alternatively probenecid, with a silicone-type adhesive or alternatively an acrylate-vinyl acetate adhesive in a solvent exemplified by methylene chloride, ethyl acetate, isopropyl myristate, and propylene glycol. The mixture would then be extruded onto a polyester-backing film to a uniform thickness of about 100 microns or greater with a precision wet-film applicator. The solvent is allowed to evaporate in a drying oven and the resulting "patch" is trimmed to the appropriate size.

The pharmaceutical for topical administration or alternatively for transdermal administration of an agent as described above (e.g., a compound selected through use of the methods disclosed herein, or alternatively, a compound selected to block a subject's pannexin-1 channels, for example the [10]panx peptide, mefloquine, probenecid, and combinations thereof) may additionally incorporate a penetration enhancer and/or a thickening agent or gelling agent and/or an emollient and/or an antioxidant and/or an antimicrobial preservative and/or an emulsifying agent and/or a water miscible solvent and/or an alcohol and/or water.

According to one aspect, the pharmaceutical composition for topical administration or transdermal administration of an agent as described above (e.g., a compound selected through use of the methods disclosed herein, or alternatively, a compound selected to block a subject's pannexin-1 channels, for example the [10]panx peptide, mefloquine, probenecid, and combinations thereof) may comprise one or more penetration enhancing agent or co-solvent for transdermal or topical delivery. A penetration enhancer is an excipient that aids in the diffusion of the active through the stratum corneum. Many penetration enhancers also function as co-solvents which are thought to increase the thermodynamic activity or solubility of the compound selected through use of the methods disclosed herein, or alternatively, a compound selected to block a subject's pannexin-1 channels, for example the [10]panx peptide, mefloquine, probenecid, and combinations thereof, in the composition. Penetration enhancers are also known as accelerants, adjuvants or sorption promoters. A suitable penetration enhancer for use in the pharmaceutical compositions and methods described herein should: (i) be highly potent, with a specific mechanism of action; (ii) exhibit a rapid onset upon administration; (iii) have a predictable duration of action; (iv) have only non-permanent or reversible effects on the skin; (v) be chemically stable; (vi) have no or minimal pharmacological effects; (vii) be physically and chemically compatible with other composition components; (viii) be odorless; (ix) be colorless; (x) be hypoallergenic; (xi) be non-irritating; (xii) be non-phototoxic; (xiii) be non-comedogenic; (xiv) have a solubility parameter approximating that of the skin (10.5 cal/cm3); (xv) be readily available; (xvi) be inexpensive; and (xvii) be able to formulated in pharmaceutical compositions for topical or transdermal delivery of an active pharmaceutical agent.

Several classes of chemical compounds, with various mechanisms of action, can be used as penetration enhancers. Set forth below are non-limiting examples of penetration enhancing agents, many of which are also suitable co-solvents. Sulfoxides, such as dimethylsulfoxide and decylmethylsulfoxide can be used as penetration enhancing agents. Dimethylsulfoxide enhances penetration in part by increasing lipid fluidity and promoting drug partitioning. In contrast, decylmethylsulfoxide enhances penetration by reacting with proteins in the skin that change the conformation of the proteins, which results in the creation of aqueous channels.

Another class of penetration enhancers are alkanones, such as N-heptane, N-octane, N-nonane, N-decane, N-undecane, N-dodecane, N-tridecane, N-tetradecane and N-hexadecane. Alkanones are thought to enhance the penetration of an active agent by altering the stratum corneum. A further class of penetration enhancers are alkanol alcohols, such as ethanol, propanol, butanol, 2-butanol, pentanol, 2-pentanol, hexanol, octanol. nonanol, decanol and benzyl alcohol. Low molecular weight alkanol alcohols, i.e., those with 6 or less carbons, may enhance penetration in part by acting as solubilizing agents, while more hydrophobic alcohols may increase diffusion by extracting lipids from the stratum corneum. A further class of penetration enhancers are fatty alcohols, such as oeyl alcohol, caprylic alcohol, decyl alcohol, lauryl alcohol, 2-lauryl alcohol, myristyl alcohol, cetyl alcohol, stearyl alcohol, oeyl alcohol, linoleyl alcohol and linolenyl alcohol. Polyols, including propylene glycol, polyethylene glycol, ethylene glycol, diethylene glycol, triethylene glycol, dipropylene glycol, glycerol, propanediol, butanediol, pentanediol, hexanetriol, propylene glycol monolaurate and diethylene glycol monomethyl ether (transcutol), can also enhance penetration. Some polyols, such as propylene glycol, may function as a penetration enhancer by solvating alpha-kertin and occupying hydrogen bonding sites, thereby reducing the amount of active-tissue binding.

Another class of penetration enhancers are amides, including urea, dimethylacetamide, diethyltoluamide, dimethylformamide, dimethyloctamide, dimethyldecamide and biodegradable cyclic urea (e.g., 1-alkyl-4-imidazolin-2-one). Amides have various mechanisms of enhancing penetration. For example, some amides, such as urea increase the hydration of the stratum corneum, act as a keratolytic and create hydrophilic diffusion channels. In contrast, other amides, such as dimethylacetamide and dimethylformamide, increase the partition to keratin at low concentrations, while increasing lipid fluidity and disrupting lipid packaging at higher concentrations. Another class of penetration enhancing agents are pyrrolidone derivatives, such as I-methyl-2-pyrrolidone, 2-pyrrolidone, 1-lauryl-2-pyrrolidone, I-methyl-4-carboxy-2-pyrrolidone, 1-hexyl-4-carboxy-2-pyrrolidone, 1-lauryl-4-carboxy-2-pyrrolidone, 1-methyl-4-methoxycarbonyl-2-pyrrolidone, 1-hexyl-4-methoxycarbonyl-2-pyrrolidone, 1-lauryl-4-methoxycarbonyl-2-pyrrolidone, N-methyl-pyrrolidone, N-cyclohexylpyrrolidone, N-dimethylaminopropyl-pyrrolidone, N-cocoalkypyrrolidone and N-tallowalkypyrrolidone, as well as biodegradable pyrrolidone derivatives, including fatty acid esters of N-(2-hydroxyethyl)-2-pyrrolidone. In part, pyrrolidone derivatives enhance penetration through interactions with the keratin in the stratum corneum and lipids in the skin structure. An additional class of penetration enhancers are cyclic amides, including 1-dodecylazacycloheptane-2-one also known as AZONE® (AZONE is a registered trademark of Echo Therapeutics Inc., Philadelphia, Pa., USA), 1-geranylazacycloheptan-2-one, 1-farnesylazacycloheptan-2-one, 1-geranylgeranylazacycloheptan-2-one, I-(3,7-dimethyloctyl)-azacycloheptan-2-one, 1-(3,7,11-trimefhyldodecyl)azacyclohaptan-2-one, 1-geranylazacyclohexane-2-one, 1-geranylazacyclopentan-2,5-dione and 1-famesylazacyclopentan-2-one. Cyclic amides, such as AZONE®, enhance the penetration of active agents in part by affecting the stratum corneum's lipid structure, increasing partitioning and increasing membrane fluidity.

Additional classes of penetration enhancers include diethanolamine, triethanolamine and hexamethylenlauramide and its derivatives.

Additional penetration enhancers include linear fatty acids, such as octanoic acid, linoleic acid, valeric acid, heptanoic acid, pelagonic acid, caproic acid, capric acid, lauric acid, myristric acid, stearic acid, oleic acid and caprylic acid. Linear fatty acids enhance penetration in part via selective perturbation of the intercellular lipid bilayers.

In addition, some linear fatty acids, such as oleic acid, enhance penetration by decreasing the phase transition temperatures of the lipid, thereby increasing motional freedom or fluidity of the lipids. Branched fatty acids, including isovaleric acid, neopentanoic acid, neoheptanoic acid, nonanoic acid, trimethyl hexaonic acid, neodecanoic acid and isostearic acid, are a further class of penetration enhancers. An additional class of penetration enhancers are aliphatic fatty acid esters, such as ethyl oleate, isopropyl n-butyrate, isopropyl n-hexanoate, isopropyl n-decanoate, isopropyl myristate ("IPM"), isopropyl palmitate and octyldodecyl myristate. Aliphatic fatty acid esters enhance penetration by increasing diffusivity in the stratum corneum and/or the partition coefficient. In addition, certain aliphatic fatty acid esters, such as IPM, enhance penetration by directly acting on the stratum corneum and permeating into the liposome bilayers thereby increasing fluidity. Alkyl fatty acid esters, such as ethyl acetate, butyl acetate, methyl acetate, methyl valerate, methyl propionate, diethyl sebacate, ethyl oleate, butyl stearate and methyl laurate, can act as penetration enhancers. Alkyl fatty acid esters enhance penetration in part by increasing the lipid fluidity.

An additional class of penetration enhancers are anionic surfactants, including sodium laurate, sodium lauryl sulfate and sodium octyl sulfate. Anionic surfactants enhance penetration of active agents by altering the barrier function of the stratum corneum and allowing removal of water-soluble agents that normally act as plasticizers. A further class of penetration enhancers are cationic surfactants, such as cetyltrimethylammonium bromide, tetradecyltrimethylammonium, octyltrimethyl ammonium bromide, benzalkonium chloride, octadecyltrimethylammonium chloride, cetylpyridinium chloride, dodecyltrimethylammonium chloride and hexadecyltrimethylammonium chloride. Cationic surfactants enhance penetration by adsorbing at, and interacting with, interfaces of biological membranes, resulting in skin damage. A further class of penetration enhancers are zwitterionic surfactants, such as hexadecyl trimethyl ammoniopropane sulfonate, oeyl betaine, cocamidopropyl hydroxysultaine and cocamidopropyl betaine. Nonionic surfactants exemplified by Polyxamer 231, Polyxamer 182, Polyxamer 184, Polysorbate 20, Polysorbate 60, BRIJ® 30, BRIJ® 93, BRIJ® 96, BRIJ® 99 (BRIJ is a registered trademark of Brij Image & Information Inc., Greensboro, N.C., USA), SPAN® 20, SPAN® 40, SPAN® 60, SPAN® 80, SPAN® 85 (SPAN is a registered trademark of Croda International PLC, East Yorkshire, UK), TWEEN® 20, TWEEN® 40, TWEEN® 60, TWEEN® 80 (TWEEN is a registered trademark of Uniqema Americas LLC, Wilmington, Del., USA), Myrj 45, MYRJ® 51, MYRJ® (MYRJ is a registered trademark of Uniqema Americas LLC, Wilmington, Del., USA), and MIGLYOL® 840 (MIGLYOL is a registered trademark of Cremer Oleo GMBH & Co., Hamburg, Fed. Rep. Germany), and the like. Nonionic surfactants enhance penetration in part by emulsifying the sebum and enhancing the thermodynamic activity or solubility of the active.

Another class of penetration enhancer increase the thermodynamic activity or solubility of the active, which include, but are not limited to, n-octanol, sodium oleate, D-limonene, monoolein, cineol, oeyl oleate, and isopropyl myristate.

Other penetration enhancers are bile salts, such as sodium cholate, sodium salts of taurocholic acid, glycolic acids and desoxycholic acids. Lecithin also has been found to have penetration enhancing characteristics. An additional class of penetration enhancers are terpenes, which include hydrocarbons, such as d-limonene, alpha-pinene and beta-carene; alcohols, such as, alpha-terpineol, terpinen-4-ol and carvol; ketones, such ascarvone, pulegone, piperitone and menthone; oxides, such as cyclohexene oxide, limonene oxide, alpha-pinene oxide, cyclopentene oxide and 1,8-cineole; and oils such as ylang ylang, anise, chenopodium and eucalyptus. Terpenes enhance penetration in part by disrupting the intercellular lipid bilayer to increase diffusivity of the active and opening polar pathways within and across the stratum corneum. Organic acids, such as salicylic acid and salicylates (including their methyl, ethyl and propyl glycol derivates), citric acid and succinic acid, are penetration enhancers. Another class of penetration enhancers are cyclodextrins, including 2-hydroxypropyl-beta-cyclodextrin and 2,6-dimethyl-beta-cyclodextrin. Cyclodextrins enhance the permeation of active agents by forming inclusion complexes with lipophilic actives and increasing their solubility in aqueous solutions.

The penetration enhancing agent(s) and/or co-solvent(s) is/are present in the pharmaceutical composition for topical administration or transdermal administration of an agent as described above (e.g., a compound selected through use of the methods disclosed herein, or alternatively probenecid) in an amount sufficient to provide the desired level of drug transport through the stratum corneum and epidermis or to increase the thermodynamic activity or solubility of the compound selected through use of the methods disclosed herein, or alternatively probenecid. The one or more pharmaceutically acceptable penetration enhancer and/or co-solvent may be present in a total amount by weight of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9% or about 10%, about 11%, about 12%, about 13%, about 14%, about 15%, about 16%, about 17%, about 18%, about 1%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

The selected penetration enhancer should be pharmacologically inert, non-toxic, and non-allergenic, have rapid and reversible onset of action, and be compatible with the compositions of the invention. Examples of penetration enhancers exemplified by transcutol P, ethyl alcohol, isopropyl alcohol, lauryl alcohol, salicylic acid, octolyphenylpolyethylene glycol, polyethylene glycol 400, propylene glycol, N-decylmethylsulfoxide, DMSO and azacyclo compounds.

In one exemplary embodiment, the present disclosure pertains to compositions for local administration of the compound selected through use of the methods disclosed herein, or alternatively, a compound selected to block a subject's pannexin-1 channels, for example the $^{10}$panx peptide, mefloquine, probenecid, and combinations thereof, in a pharmaceutically sufficient amount to treat peripheral neuropathy. As used herein, the term "local" refers to the limited area near the site of administration, generally the nerves at or near skin including the epidermis, the dermis, the dermatomes and the like, with no or limited systemic penetration beyond the skin.

Preferably, the topical delivery is designed to maximize drug delivery through the stratum corneum and into the epidermis or dermis or dermatome, and to minimize absorption into the circulatory system. More preferable are agents that may be used in topical formulations to prevent the passage of active ingredients or excipients into the lower skin layers. These so-called skin retardants have been readily developed for many over-the-counter (OTC) skin formulations, such as sunscreens and pesticides, where the site of action is restricted to the skin surface or upper skin layers. Research in the area of permeation enhancement or retardation is yielding valuable insights into the structure—activity relationships of enhancers as well as retardants (Asbill et al., 2000, *Percutaneous penetration enhancers: local versus transdermal activity*. Pharm. Sci. Tech. Today, 3(1):36-41; Kaushik, et al., 2008, *Percutaneous permeation modifiers: enhancement versus retardation*. Exp. Opin. Drug Del. 5(5):517-529; Trommer et al., 2006, *Overcoming the Stratum Corneum: The Modulation of Skin Penetration*. Skin Pharmacol. Physiol. 19:106-121) including such compounds as ketorolac stearate, Aminocaprolactam Analogues, Dicarboxylic acid ester, sodium citrate, and the like.

The compositions described herein can further comprise components usually admixed in such preparations. For example, the compositions may also include additional ingredients such as other carriers, moisturizers, oils, fats, waxes, surfactants, thickening agents, antioxidants, viscosity stabilizers, chelating agents, buffers, preservatives, perfumes, dyestuffs, lower alkanols, humectants, emollients, dispersants, sunscreens such as radiation blocking compounds or particularly UV-blockers, antibacterials, antifungals, disinfectants, vitamins, antibiotics, or other anti-acne agents, as well as other suitable materials that do not have a significant adverse effect on the activity of the topical composition. Additional ingredients for inclusion in the carrier are sodium acid phosphate moisturizer, witch hazel extract carrier, glycerin humectant, apricot kernel oil emollient, corn oil dispersant, and the like which are further detailed below. Those of skill in the art will readily recognize additional ingredients, which can be admixed in the compositions described herein.

According to another aspect, the pharmaceutical composition for topical administration or for transdermal application of a compound selected through use of the methods disclosed herein, or alternatively probenecid, may comprise a thickening or gelling agent suitable for use in the compositions and methods described herein to increase the viscosity of the composition. Suitable agents (also known as gelling agents) are exemplified neutralized anionic polymers or neutralized carbomers, such as polyacrylic acid, carboxypolymethylene, carboxymethyl cellulose and the like, including derivatives of Ultrez 10, CARBOPOL® polymers, such as CARBOPOL® 940, CARBOPOL® 941, CARBOPOL® 954, CARBOPOL® 980, CARBOPOL® 981, CARBOPOL® ETD 2001, CARBOPOL® EZ-2 and CARBOPOL® EZ-3. (CARBOPOL is a registered trademark of Lubrizol Advanced Materials Inc., Cleveland, Ohio, USA). As used herein, a "neutralized carbomer" is a synthetic, high molecular weight polymer, composed primarily of a neutralized polyacrylic acid. Further, when a base is added to neutralize a carbomer solution, the viscosity of the solution increases. Also suitable are other known polymeric thickening agents, such as PEMULEN® polymeric emulsifiers, NOVEON® polycarbophils (PEMULEN and NOVEON are registered trademarks of Lubrizol Advanced Materials Inc.), and KLUCEL® (KLUCEL is a registered trademark of Hercules Inc., Wilmington, Del., USA). Additional thickening agents, enhancers and adjuvants may generally be found in Remington's The Science and Practice of Pharmacy as well as in the Handbook of Pharmaceutical Excipients (Arthur H. Kibbe ed. 2000). Alternatively, the pharmaceutical composition for topical administration or for transdermal application of a compound selected through use of the methods disclosed herein, or alternatively probenecid, may comprise an anionic polymer thickening agent precursor, such as a carbomer, which has been combined with a neutralizer in an amount sufficient to form a gel or gel-like composition with a viscosity greater than 1000 cps as measured by a Brookfield RV DVII+ Viscometer with spindle CPE-52, torque greater than 10% and the temperature maintained at 25° C. Alternatively, the anionic polymer thickening agent precursor may be combined with a neutralizer selected from the group consisting of: sodium hydroxide, ammonium hydroxide, potassium hydroxide, arginine, aminomethyl propanol, tetrahydroxypropyl ethylenediamine, triethanolamine ("TEA"), tromethamine, PEG-15 cocamine, diisopropanolamine, and triisopropanolamine, or combinations thereof in an amount sufficient to neutralize the anionic polymer thickening agent precursor to form a gel or gel-like composition in the course of forming the composition. The thickening agents or gelling agents are present in an amount sufficient to provide the desired rheological properties of the composition, which include having a sufficient viscosity for forming a gel or gel-like composition that can be applied to the skin of a mammal. The thickening agent or gelling agent is present in a total amount by weight of about 0.1%, about 0.25%, about 0.5%, about 0.75%, about 1%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, about 7.5%, about 7.75%, about 8.0%, about 8.25%, about 8.5%, about 8.75%), about 9.0%, about 9.25%, about 9.5%, about 9.75%, about 10%, about 11%, about 11.5%, about 12%, about 12.5%, about 13%, about 13.5%, about 14%, about 14.5% or about 15%, and therebetween.

According to another aspect, the pharmaceutical composition for topical administration or for transdermal application of a compound selected through use of the methods disclosed herein, or alternatively, a compound selected to block a subject's pannexin-1 channels, for example the $^{10}$panx peptide, mefloquine, probenecid, and combinations thereof, may comprise an emollient. Suitable emollients are exemplified by mineral oil, mixtures of mineral oil and lanolin alcohols, cetyl alcohol, cetostearyl alcohol, petrolatum, petrolatum and lanolin alcohols, cetyl esters wax, cholesterol, glycerin, glyceryl monostearate, isopropyl myristate, isopropyl palmitate, lecithin, allyl caproate, althea officinalis extract, arachidyl alcohol, argobase EUC, butylene glycol, dicaprylate/dicaprate, acacia, allantoin, carrageenan, cetyl dimethicone, cyclome hicone, diethyl succinate, dihydroabietyl behenate, dioctyl adipate, ethyl laurate, ethyl palmitate, ethyl stearate, isoamyl laurate, octanoate, PEG-75, lanolin, sorbitan laurate, walnut oil, wheat germ oil, super refined almond, super refined sesame, super refined soybean, octyl palmitate, caprylic/capric triglyceride and glyceryl cocoate. An emollient, if present, is present in the compositions described herein in an amount by weight of the composition of about 1% to about 30%, about 3% to about 25%, or about 5% to about 15%. Illustratively, one or more emollients are present in a total amount of about 1% by weight, about 2%, about 3%, about 4%, about 5%, about 6%, about 7%, about 8%, about 9%, about 10%, about 11%, about 12%, about 13%, about 14%, about 1%, about 16%, about 17%, about 18%, about 19%, about 20%, about 21%, about 22%, about 23%, about 24%, about 25%, about 26%, about 27%, about 28%, about 29%, or about 30%, and therebetween.

According to another aspect, the pharmaceutical composition for topical administration or for transdermal application of a compound selected through use of the methods disclosed herein, or alternatively, a compound selected to block a subject's pannexin-1 channels, for example the $^{10}$panx peptide, mefloquine, probenecid, and combinations thereof, may comprise an antioxidant. Suitable antioxidants are exemplified by citric acid, butylated hydroxytoluene (BHT), ascorbic acid, glutathione, retinol, α-tocopherol, β-carotene, α-carotene, ubiquinone, butylated hydroxyanisole, ethyl enediaminetetraacetic acid, selenium, zinc, lignan, uric acid, lipoic acid, and N-acetylcysteine. An antioxidant, if present, is present in the compositions described herein in a total amount selected from the range of about 0.025% to about 1.0% by weight.

According to another aspect, the pharmaceutical composition for topical administration or for transdermal application of a compound selected through use of the methods disclosed herein or alternatively, a compound selected to block a subject's pannexin-1 channels, for example the $^{10}$panx peptide, mefloquine, probenecid, and combinations thereof, may comprise an antimicrobial preservative. Illustrative anti-microbial preservatives include acids, including but not limited to, benzoic acid, phenolic acid, sorbic acids, alcohols, benzethonium chloride, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, propylparaben, sodium propionate or thimerosal. The anti-microbial preservative, if present, is present in an amount by weight of the composition of about 0.1% to about 5%, about 0.2% to about 3%, or about 0.3% to about 2%, for example about 0.2%, about 0.4%, about 0.6%, about 0.8%, about 1%, about 1.2%, about 1.4%, about 1.6%, about 1.8%, about 2%, about 2.2%, about 2.4%, about 2.6%, about 2.8%, about 3.0%, about 3.2%, about 3.4%, about 3.6%, about 3.8%, about 4%, about 4.2%, about 4.4%, about 4.6%, about 4.8%, or about 5%.

According to another aspect, the pharmaceutical composition for topical administration or for transdermal application of a compound selected through use of the methods disclosed herein, or alternatively, a compound selected to block a subject's pannexin-1 channels, for example the $^{10}$panx peptide, mefloquine, probenecid, and combinations thereof, may comprise one or more emulsifying agents. The term "emulsifying agent" refers to an agent capable of lowering surface tension between a non-polar and polar phase and includes self emulsifying agents. Suitable emulsifying agents can come from any class of pharmaceutically acceptable emulsifying agents exemplified by carbohydrates, proteins, high molecular weight alcohols, wetting agents, waxes and finely divided solids. The optional emulsifying agent, if present, is present in a composition in a total amount of about 1% to about 25%, about 1% to about 20%, or about 1% to about 15% by weight of the composition. Illustratively, one or more emulsifying agents are present in a total amount by weight of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25%.

According to another aspect, the pharmaceutical composition for topical administration or for transdermal application of a compound selected through use of the methods disclosed herein, or alternatively, a compound selected to block a subject's pannexin-1 channels, for example the $^{10}$panx peptide, mefloquine, probenecid, and combinations thereof, may comprise a water-miscible solvent exemplified by propylene glycol. A suitable water-miscible solvent refers to any solvent that is acceptable for use in a pharmaceutical composition and is miscible with water. If present, the water-miscible solvent is present in a composition in a total amount of about 1% to about 95%, about 2% to about 75%, about 3% to about 50%, about 4% to about 40%, or about 5% to about 25% by weight of the composition.

According to another aspect, the pharmaceutical composition for topical administration or for transdermal application of a compound selected through use of the methods disclosed herein, or alternatively, a compound selected to block a subject's pannexin-1 channels, for example the $^{10}$panx peptide, mefloquine, probenecid, and combinations thereof, may comprise one or more alcohols. In a further embodiment, the alcohol is a lower alcohol. As used herein, the term "lower alcohol," alone or in combination, means a straight-chain or branched-chain alcohol moiety containing one to about six carbon atoms. In one embodiment, the lower alcohol contains one to about four carbon atoms, and in another embodiment the lower alcohol contains two or three carbon atoms. Examples of such alcohol moieties include methanol, ethanol, ethanol USP (i.e., 95% v/v), n-propanol, isopropanol, n-butanol, isobutanol, sec-butanol, and tert-butanol.

As used herein, the term "ethanol" refers to C2H5OH. It may be used as dehydrated alcohol USP, alcohol USP or in any common form including in combination with various amounts of water. If present, the alcohol is present in an amount sufficient to form a composition which is suitable for contact with a mammal. For example, in a total amount by weight of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%.

Another embodiment pertains to pharmaceutical compositions comprising a compound selected through use of the methods disclosed herein, or alternatively, a compound selected to block a subject's pannexin-1 channels, for example the $^{10}$panx peptide, mefloquine, probenecid, and combinations thereof, formulated for parenteral administration by injection. The injectable pharmaceutical compositions of the present disclosure comprise a suitable carrier solution exemplified by sterile water, saline, and buffered solutions at physiological pH. Suitable buffered solutions are exemplified by Ringer's dextrose solution and Ringer's lactated solutions. The carrier solution may comprise in a total amount by weight of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%>, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%>, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%), about 9.3%, about 9.4%, about 9.5%, about 9.6%, about 9.7%, about 9.8%, about 9.9% or about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%», about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

According to one aspect, the injectable pharmaceutical compositions may additionally incorporate one or more non-aqueous solvents exemplified by propylene glycol, polyethylene glycol, vegetable oils such as olive oil, and injectable organic esters exemplified by ethyl oleate.

According to another aspect, the injectable pharmaceutical compositions may additionally incorporate one or more of antimicrobials, anti-oxidants, chelating agents and the like.

The injectable pharmaceutical compositions may be presented in unit-dose or multi-dose containers exemplified by sealed ampules and vials. The injectable pharmaceutical compositions may be stored in a freeze-dried (lyophilized) condition requiring the addition of a sterile liquid carrier, e.g., sterile saline solution for injections, immediately prior to use.

Another embodiment pertains to pharmaceutical compositions comprising a compound selected through use of the methods disclosed herein, or alternatively, a compound selected to block a subject's pannexin-1 channels, for example the $^{10}$panx peptide, mefloquine, probenecid, and combinations thereof, formulated for oral administration. The oral pharmaceutical compositions may be provided as capsules or tablets; as powders or granules; as solutions, syrups or suspensions (in aqueous or non-aqueous liquids). Tablets or hard gelatine capsules may comprise, for example, lactose, starch or derivatives thereof, magnesium stearate, sodium saccharine, cellulose, magnesium carbonate, stearic acid or salts thereof. Soft gelatine capsules may comprise, for example, vegetable oils, waxes, fats, semisolid, or liquid polyols, etc. Solutions and syrups may comprise, for example, water, polyols and sugars. The compound selected through use of the methods disclosed herein, or alternatively probenecid, may be coated with or admixed with a material (e.g., glyceryl monostearate or glyceryl distearate) that delays disintegration or affects absorption of the active agent in the gastrointestinal tract. Thus, for example, the sustained release of an active agent may be achieved over many hours and, if necessary, the active agent can be protected from being degraded within the gastrointestinal tract. Taking advantage of the various pH and enzymatic conditions along the gastrointestinal tract, pharmaceutical compositions for oral administration may be formulated to facilitate release of an active agent at a particular gastrointestinal location.

The following examples are provided to more fully describe the disclosure and are presented for non-limiting illustrative purposes.

EXAMPLES

The following methods and materials were used in the examples disclosed herein.

Animals:

Adult male rats and mice were used (rats aged 7-8 weeks; mice aged 6-10 weeks). Mice and rats were housed under 12-h/12-h light/dark cycle with ad libitum access to food and water. All experiments were approved by the University of Calgary and Université Laval Animal Care Committee and are in accordance with the guidelines of the Canadian Council on Animal Care.

Morphine Dosing Paradigm and Nociceptive Behavioral Models:

Morphine sulfate (PCCA) prepared in 0.9% sterile saline solution was injected intraperitoneally twice daily (8 a.m. and 5 p.m.) into Sprague-Dawley rats (escalating doses from 10 to 45 mg per kg), Cx3cr1-cre::Pnx1$^{flx/flx}$, or Pnx1$^{flx/flx}$ mice (escalating doses from 7.5 to 50 mg per kg). Thermal nociceptive thresholds were assessed using the tail-flick test (rats) and the tail-immersion test (mice). For rats, an infrared thermal stimulus (Ugo Basile) was applied to the ventral surface of the tail and time latency for tail removal from the stimulus was recorded. For mice, the distal portion of the tail was submerged in a 50° C. water bath and time latency for tail removal from the stimulus was recorded. A maximum cut-off time was set for 10 s to prevent tissue damage. Nociceptive measurements were taken prior to and 30 minutes after morphine injections and values were normalized to daily baseline. In a subset of mouse experiments, a time-course of morphine-induced antinociception was performed at 30 min, 45 min, 60 min, 120 min, and 180 min after a single acute injection of morphine (7.5 mg per kg).

Behavioral Assessment of Naloxone-Precipitated Morphine Withdrawal:

Rats and mice received ascending doses of morphine intraperitoneally at 8-h intervals (rats: day 1, 10 mg per kg; day 2, 20 mg per kg; day 3, 30 mg per kg; day 4, 40 mg per kg; mice: day 1, 7.5 and 15 mg per kg; day 2, 20 and 25 mg per kg; day 3, 30 and 35 mg per kg; day 4, 40 and 45 mg per kg). On day 5, rats and mice received a morning injection morphine (rats: 45 mg per kg; mice: 50 mg per kg) and 2 hours later naloxone (2 mg per kg) to rapidly precipitate withdrawal. Control rats and mice received saline and were challenged with naloxone on day 5. Signs of withdrawal were recorded following the methods taught by Ferrini et al (2013, *Morphine hyperalgesia gated through microglia-mediated disruption of neuronal Cl$^-$ homeostasis*. Nat. Neurosci. 16:183-192). Jumping, teeth chattering, wet-dog shakes, headshakes, and grooming behaviors were evaluated at 5-min intervals for a total test period of 30 minutes and a standardized score of 0 to 3 was assigned to each behavior. Allodynia, piloerection, salivation, ejaculation, and tremor-sitwitchina were also evaluated, with one point given to the presence of the behavior during each 5-min interval. All signs were counted and compiled to yield a cumulative withdrawal score. Rats and mice were weighed before and after naloxone challenge to calculate weight loss. In all behavioral studies, experimenters were blind to the drug treatments and genetic profile of rats and mice.

Intrathecal Drug Administration:

In a subset of experiments, rats and mice were subject to drug administration by intrathecal injection under 2% isoflurane (vol/vol) by lumbar puncture method as taught by Ichikizaki et al. (1979, *A new procedure for lumbar puncture in the mouse (intrathecal injection) preliminary report*. Keio J. Med. 28(4): 165-171). Mac-1-saporin and saporin (20 μg, Advanced Targeting Systems) were injected on day 1 and day 3 before morning morphine injections. Intrathecal injections of $^{10}$panx (10 μg, WRQAAFVDSY, SEQ ID NO: 1) and $^{scr}$panx (10 μg, FSVYWAQADR, SEQ ID NO: 2) were delivered 1 h prior to naloxone-precipitated withdrawal, while intrathecal apyrase (10 units, Sigma Aldrich) and ARL67156 (10 nmoles, Sigma Aldrich) were delivered 15 minutes prior to naloxone. ATPyS (100 μM, Roche) was delivered immediately prior to naloxone-precipitated withdrawal. All control animals received intrathecal saline. Some rats were subject to intrathecal drug delivery by micro-osmotic pump implantation (Alzet). Rats were anaesthetized with 2% isoflurane (vol/vol) and a catheter connected to a micro-osmotic pump was inserted into the dorsal intrathecal space of the lumbar segment. Osmotic pumps provided continuous drug delivery (1 μL per hour) from day 1 to day 4 of morphine or saline treatment, and were filled with saline, $^{10}$panx (2 μg per μL) or $^{scr}$panx (2 μg per μL).

Systemic Drug Administration:

Morphine dependent rats received systemic mefloquine (45 mg per kg i.p., Sigma) or probenecid (50 mg per kg i.p., Sigma) 1 hour prior to naloxone-precipitated withdrawal. Both mefloquine and probenecid were reconstituted in β-cyclodextrin (Sigma), and control animals received systemic β-cyclodextrin.

Western blotting:

Rat spinal cord tissue was rapidly dissected and homogenized in RIPA buffer containing 20 mM TrisHCl (pH 7.5), 150 mM NaCl, and 0.5% Tween-20. Cultured microglia were harvested in 150 μL lysis buffer containing 50 mM TrisHCl, 150 mM NaCl, 10 mM EDTA, 0.1% Triton-X, and 5% Glycerol. Both RIPA and lysis buffers contained protease inhibitors (Sigma) and phosphatase inhibitors (GBiosciences). Total protein was measured using a BioRad RC DC Protein Assay Kit (BioRad) or Pierce BCA Protein Assay Kit (Thermo Scientific). Samples were heated at 95° C. for 5-min in loading buffer (350 mM Tris, 30% glycerol, 1.6% SDS, 1.2% bromophenol blue, 6% β-mercaptoethanol) then electrophoresed on a precast SDS gel (4-12% Tris-HCl, BioRad) and transferred onto a nitrocellulose membrane. After blocking, membranes were incubated with rabbit antibody to P2X7R (1:300, Alomone, APR008), mouse antibody to β-Actin (1:2000, Sigma-Aldrich, A5316), or rabbit antibody to Panx1 (1:300, Life Technologies, 488100; or 1:10, 000, Abcam, ab124969). Membranes were washed and incubated for 2 h at 20-25° C. in fluorophore-conjugated secondary antibodies (anti-rabbit and anti-mouse conjugated IR Dyes 1:5000, Mandel Scientific; or Fluorescent TrueBlot anti-rabbit IgG Dylight 1:1000, Rockland) then quantified by direct detection of secondary antibody fluorescence at 680 and 800 nm (LICOR Odyssey CLx). Band intensity was quantified using Image J, normalized to β-actin and expressed relative to control samples.

Isolation of Adult Mixed Neuron-Glia Culture:

Rats and mice were anaesthetized and perfused transcardially with PBS only. Spinal cord and brain (mice only) tissue was isolated and placed in PBS containing 10% FBS. Following blunt dissociation, spinal cord contents were filtered through a 70 μm cell strainer into DMEM containing 10 mM HEPES and 2% FBS. Isotonic percoll (density 1.23 g/mL) was added to the cell suspension, followed by a 1.08 g per mL percoll underlay. Samples were spun at 3,000 rpm for 30 minutes at 20° C. Following centrifugation, myelin debris was removed and the interface between percoll gradients was collected and transferred into fresh media. Samples were re-spun at 1,350 rpm for 10 minutes at 4° C. and the pellet was reconstituted in PBS containing 10% FBS for flow cytometry or DMEM containing 10% FBS and 1% Pen-Strep for live-cell imaging.

Flow Cytometry:

Mixed neuron-glia culture was isolated from adult rat spinal cord as described above. Cells were stained with antibodies Panx1 (1:400 Pierce, Life Technologies) and fluorophore-conjugated antibody CD11b/c-PE (1:500 eBioscience) for 1 hour at 20° C. Cell fluorescence was measured by an Attune Acoustic Focusing Cytometer (Applied Biosystems). Live single cell population was gated using forward and side scatter plot. CD11b and Panx1 positive staining was gated using BL2 and RL1 intensities respectively, in single stained cells compared to unstained cells.

BV2 Microglia Culture:

BV2 microglia were maintained in DMEM media (Gibco) containing 10% FBS and 1% Pen-Strep at 37° C. with 5% $CO_2$. Cells were treated with morphine (10 μM) or saline once a day for 5 days.

Primary Microglia Culture from Postnatal Rats:

Primary microglia cultures were prepared as taught by Trang et al. (2009, *P2X4-receptor-mediated synthesis and release of brain-derived neurotrophic factor in microglia is dependent on calcium and p38-mitogen-activated protein kinase activation*. J. Neurosci. 18; 29(11):3518-3528). In brief, mixed neuron-glia culture was isolated from postnatal (P1-P3) Sprague Dawley rat cortex and maintained for 10-14 days in DMEM medium containing 10% FBS and 1% Pen-Strep at 37° C. with 5% $CO_2$. Microglia were separated from the mixed culture by gentle shaking. Following isolation, microglia were plated and treated with morphine (10 μM) or saline once a day for 5 days.

Calcium Imaging:

Cells were incubated for 30-min with the fluorescent $Ca^{2+}$ indicator dye Fura-2 AM (2.5 µM, Molecular Probes) in extracellular solution (ECS) containing 140 mM NaCl, 5.4 mM KCl, 1.3 mM $CaCl_2$, 10 mM HEPES, and 33 mM glucose (pH 7.35, osmolarity 315 mOsm). All experiments were conducted at room temperature using an inverted microscope (Nikon Eclipse Ti C1SI Spectral Confocal) and the fluorescence of individual microglia was recorded using EasyRatioPro software (PTI). Excitation light was generated from a xenon arc lamp and passed alternatingly through 340 or 380 nm bandpass filters (Omega Optical, VT, USA). The 340/380 fluorescence ratio was calculated after baseline subtraction.

Generation of Cx3cr1::Panx1$^{flx/flx}$ Mice:

Mice with microglial specific deletion of Panx1 were generated using a Cre-loxP system. Panx1$^{flx/flx}$ homozygote mice (Weillenger et al., 2012, *Anoxia-induced NMDA receptor activation opens pannexin channels via Src family kinases*. J. Neurosci. 32(36):12579-12588) containing flox sequences flanking exon 2 of the Panx1 gene were crossed with C57BL6/J mice expressing Cre-ER fusion protein and enhanced yellow fluorescent protein (eYFP) under the Cx3cr1 promoter (Jax mice: B6.129P2(Cg)-Cx3cr1$^{tm2.1(cre/ERT)Litt}$/WganJ, stock number 021160). Progeny genotype was screened using PCR, and homozygous Panx1$^{flx/flx}$ and Cx3cr1-cre mice were bred and backcrossed for 8 generations to yield the conditional Cx3cr1::Panx1$^{flx/flx}$ knock-out mice. To induce Cre recombination, mice were injected intraperitoneally with 1 mg per day tamoxifen (Sigma) for 5 days. Wild-type mice were littermate mice that received vehicle injections (sunflower oil with 10% ethanol) for 5 days, while tamoxifen-related effects were controlled for using Panx1$^{flx/flx}$ littermate mice that received 5 days of tamoxifen injections. In the majority of experiments, testing occurred 7 days after final tamoxifen injection, and success of recombination at 7 days was assessed using Ai14 tdTomato reporter mice (Jax mice: B6.Cg-Gt(ROSA)26Sor$^{tm14(CAG-tdTomato)Hze}$/J, stock number 007914) crossed with $CX_3CR_1$-cre mice. In a subset of experiments, behavioural assessment of morphine withdrawal was conducted 28 days after final tamoxifen injection to control for effects of peripheral Cx3cr1-expressing cells.

YO-PRO Dye-Uptake:

Following 5 d morphine or saline treatment, BV-2 cells were incubated in YO-PRO-1 or YO-PRO-3 dye (2.5 µM, Invitrogen) in ECS. Following a 5-min baseline recording, cells were stimulated with BzATP (150 µM, Sigma) and dye-uptake was recorded for 30 minutes. Cell viability was assessed immediately after 30 minute recording by application of ionomycin (1 µM, Sigma). YO-PRO-1 dye fluorescent emission (491/509) or YO-PRO-3 dye fluorescent emission (612/631) was detected at 37° C. using a FilterMax F5 plate reader (Molecular Devices). Drugs used include $^{10}$panx, $^{scr}$panx, and naloxone, all of which were used at 10 µM. Drugs were bath applied in YO-PRO-1 dye and incubated at 37° C. for 10 minutes prior to baseline recording. Fluorescent emission at 30 minutes post BzATP application was calculated as percent change from baseline. Representative images of BV-2 YO-PRO-1 dye uptake were taken at room temperature using an inverted microscope (Nikon Eclipse Ti C1S1 Spectral Confocal) with images take at 5 minute intervals for 30 minutes using EasyRatioPro software (PTI). To assess Panx1 function in Cx3cr1::Panx1$^{flx/flx}$ adult microglia, neuron-glia mixture culture was isolated from adult mice treated with tamoxifen or vehicle for 5 days, then plated in DMEM containing 10% FBS and 1% Pen-Strep and incubated overnight at 37° C. with 5% $CO_2$. Cells were washed and incubated with DAPI (1:10,000) for 10 minutes, and then incubated in YO-PRO-3 dye. Microglia were identified from mixed adult neuronal-glia culture by endogenous expression of eYFP. Fluorescence of individual eYFP positive microglia was recorded for a 5 minute baseline period and then for 30 minutes post BzATP stimulation (300 µM). Fluorescent emission at 30 minutes was calculated and as percent change from baseline.

Naloxone-Stimulated ATP Release:

ATP level were detected using bioluminescence by combining samples with recombinant firefly luciferase and its substrate D-luciferin (ATP Determination Kit, Life Technologies). The ATPase inhibitor (ARL67156, 1 µM, Sigma) was added to the ECS or ACSF to decrease breakdown of ATP, and samples were incubated in medium for 30 minutes prior to naloxone stimulation to reduce mechanically-induced ATP release. Samples were stimulated with naloxone (10 µM) for 30 minutes, at which point the supernatant was collected. Samples were read immediately after collection using a FilterMax F5 plate reader at 28° C. For experiments for BV-2 microglial cultures, cells were incubated in $^{10}$panx (10 µM), $^{scr}$panx (10 µM), probenecid (1 mM), mefloquine (40 µM) or ECS for 10 minutes prior to naloxone stimulation. Final ATP measurement was expressed relative to control samples (saline treated and ECS stimulated) from the same plate. For ATP release in spinal cord slices, tamoxifen or vehicle treated Cx3cr1::Panx1$^{flx/flx}$ mice were perfused with ice-cold oxygenated sucrose-substituted ACSF, and the spinal cord isolated by hydraulic extrusion. The lumbar segment of the spinal cord was sliced into 300 µm sections, and incubated in oxygenated 37° C. ACSF for 1 hour. Spinal cord slices were then transferred to room temperature oxygenated ACSF and stimulated with naloxone. For quantification, ATP release was normalized to total protein of each sample.

Histological Procedures:

Rats and mice were anesthetized with pentobarbital (Bimeda-MTC Animal Health Inc.) and perfused transcardially with 4% paraformaldehyde (PFA) (wt/vol). Following dissection, the spinal lumbar segment was post-fixed in 4% PFA, then cryoprotected in 30% sucrose. Spinal cords were sliced at 30 µm into free-floating sections, then incubated overnight at 4° C. in mouse antibody to CD11b (1:50, CBL1512 EMD Milipore), rat antibody to CD11b (1:500, Abcam, ab64347), or rabbit antibody to GFP (1:400, Life Technologies, A-6465). Sections were then washed and incubated at 4° C. with fluorochrome-conjugated secondary antibodies (1:1000, Cy3—conjugated donkey anti-mouse IgG, Jackson Immuno Research; 1:100, Cy5—conjugated donkey anti-rabbit IgG, Jackson Immuno Research; or 1:2000 donkey anti-rat IgG AlexaFluor 555, Abcam, ab150154). Images were taken using a Nikon Eclipse Ti C1SI Spectral Confocal microscope. Quantification was performed using Image J (NIH), with experimenter blind to genotype and/or drug treatment.

c-Fos Immunolabeling:

Mouse spinal cord tissue was isolated and sectioned as stated above. Free-floating spinal cord sections were blocked for 10-min with 0.3% $H_2O_2$ and then for 5-min with 1% $NaBH_4$. Sections were incubated overnight at 4° C. with rabbit antibody to cFos (1:5000, Abcam, ab7963). Sections were washed and incubated for 2 h in biotinylated anti-rabbit secondary antibody (1:1000; Vector Laboratories Inc.) then processed with Vecastain ABC kit (Vector Laboratories Inc.) and developed for 1-min using 3,3-diaminobenzedine with nickel. Images were taken using an Olympus Virtual Slide System Macro Slide Scanner and number of Fos-immunoreactive cells within the superficial spinal dorsal horn were counted. Imaging and quantification were performed by an experimenter blind to genotype and drug treatment.

Ex-Vivo Spinal Cord Recordings:

Electrically-evoked field potentials in the superficial dorsal horn were recorded as taught by Bonin et al. (2014, *A spinal analog of memory reconsolidation enables reversal of hyperalgesia*. Nat. Neurosci.; 17(8):1043-5). Animals were anesthetized with urethane (2 g/kg) and briefly perfused transcardially with an ice-cold oxygenated (95% $O_2$, 5% $CO_2$) sucrose-based artificial cerebrospinal fluid (S-aCSF) solution containing the following (in mM): 252 sucrose, 2.5 KCl, 6 MgCl2, 1.5 CaCl2, 1.25 $NaH_2PO_4$, 26 $NaHCO_3$, 4 kynurenic acid and 10 D-glucose. The lumbar spinal column was rapidly removed and immersed in ice cold S-ACSF and the spinal cord was obtained by laminectomy. Spinal cord explants were allowed to recover for 30 minutes in an immersion chamber containing oxygenated (95% $O_2$, 5% $CO_2$) aCSF (126 NaCl, 2.5 KCl, 2 $MgCl_2$, 2 $CaCl_2$, 1.25 $NaH_2PO_4$, 26 $NaHCO_3$, and 10 D-glucose) at room temperature.

Postsynaptic field potentials (fPSPs) were recorded via a borosilicate glass electrode inserted into the dorsal side of the spinal cord explant in the dorsal root entry zone. Electrodes were inserted superficially to a depth of no more than 125 µm from the dorsal surface of the spinal cord measured with an MPC-200 manipulator (Sutter Instrument Company, Novato, Calif., USA). Electrodes had a tip resistance of 3-4 MΩ when filled with aCSF. fPSPs were evoked by electrical stimulation of the dorsal root using an aCSF-filled borosilicate suction electrode placed near the cut end of the dorsal root. Field potentials were amplified with a Multiclamp 700B amplifier (Molecular Devices, Sunnyvale, Calif., USA), digitized with a Digidata 1322A (Molecular Devices), and recorded using pClamp 10 software (Molecular Devices). Data were filtered during acquisition with a low pass filter set at 1.6 kHz and sampled at 10 kHz. Test stimuli were presented every 60 s to evoke fPSPs and baseline was determined as a 30-minute period of stable responses (less than 15% variability). After a stable baseline was observed, naloxone (10 µM) was applied via the bath or LTP was evoked by stimulation at 2 Hz for 2 minutes with a 25% higher intensity than baseline stimulation, after which stimulation was retuned to baseline levels and test pulses were again delivered once per minute. Data were analyzed using ClampFit 10 software (Molecular Devices). The area of fPSPs relative to baseline was measured from 0-800 ms after the onset of the fPSP.

Statistics:

All data are presented as the mean±s.e.m. Tests of statistical difference were performed using unpaired t test (2-sided), or ordinary one-way ANOVA with post hoc Bonferroni or Sidak's test. Time course and daily antinociception experiments were analyzed using a two-way repeated measure ANOVA with post-hoc Sidak. Samples sizes are consistent with those reported in similar studies. For all experiments, a criterion a level was set at 0.05.

Figure 1:
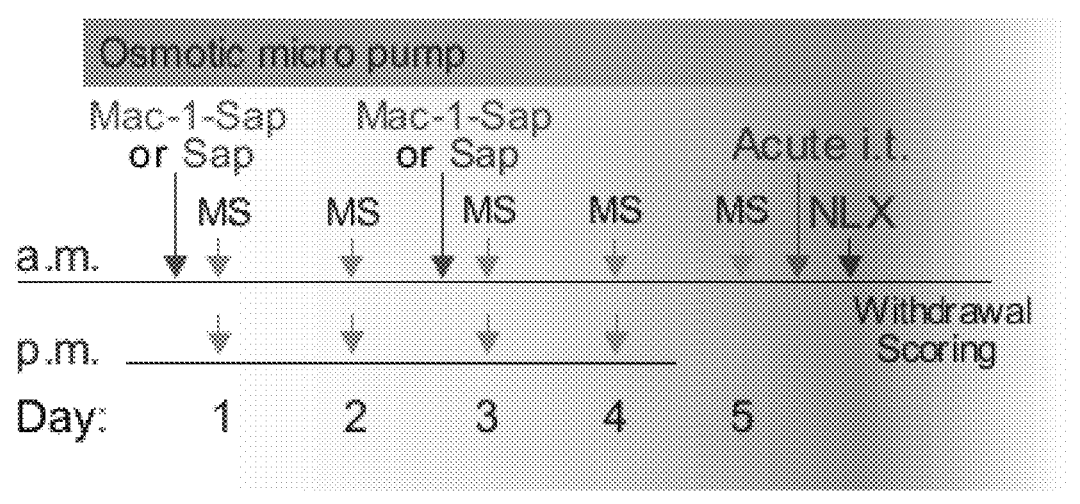
Figure 3:
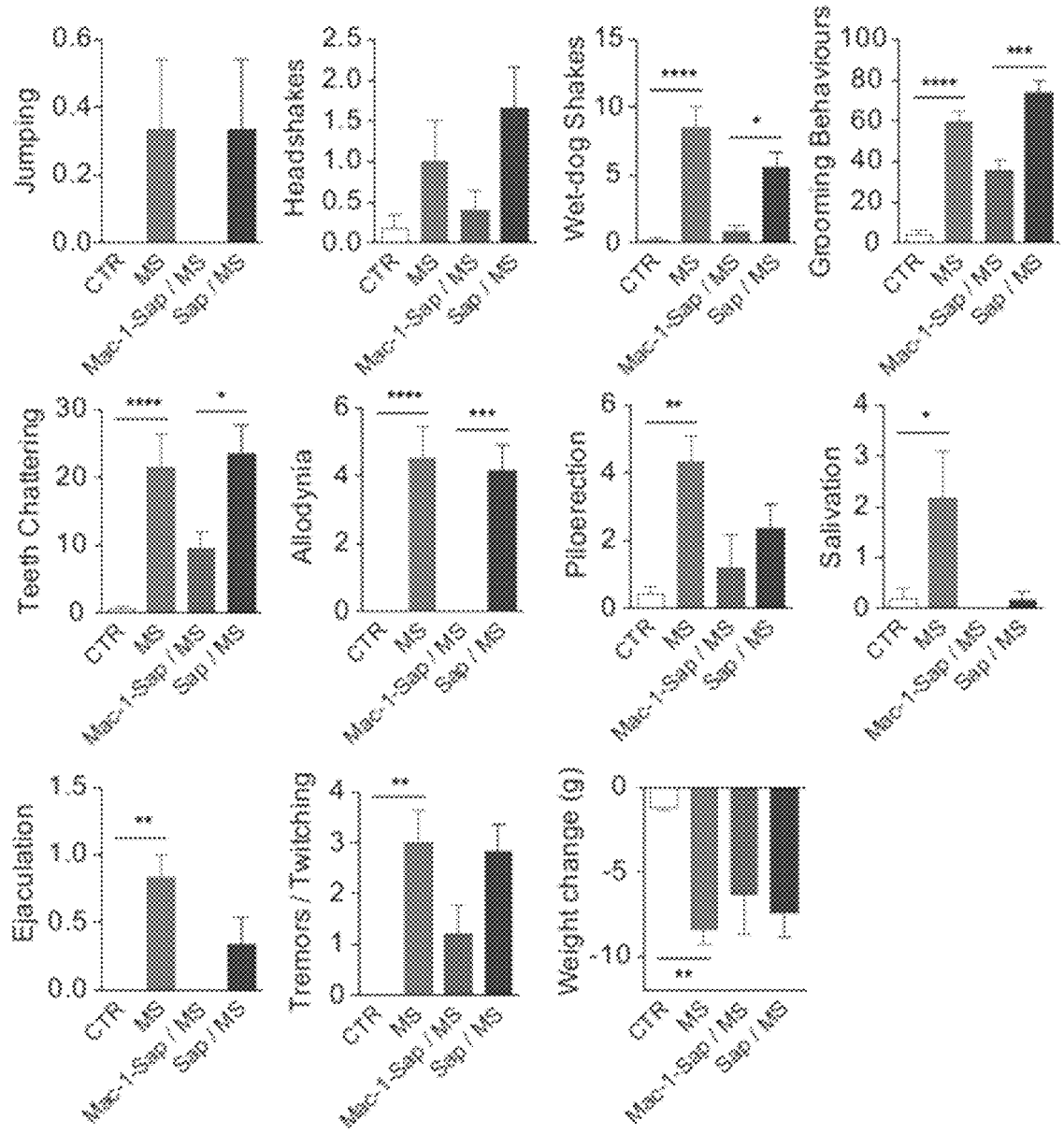
FIG. 3 is a series of charts showing the effects of intrathecal saline, saporin, or Mac-1-saporin injections on somatic and autonomic withdrawal behaviors in control animals (saline treated) animals and in morphine treated animals.
Figure 4:
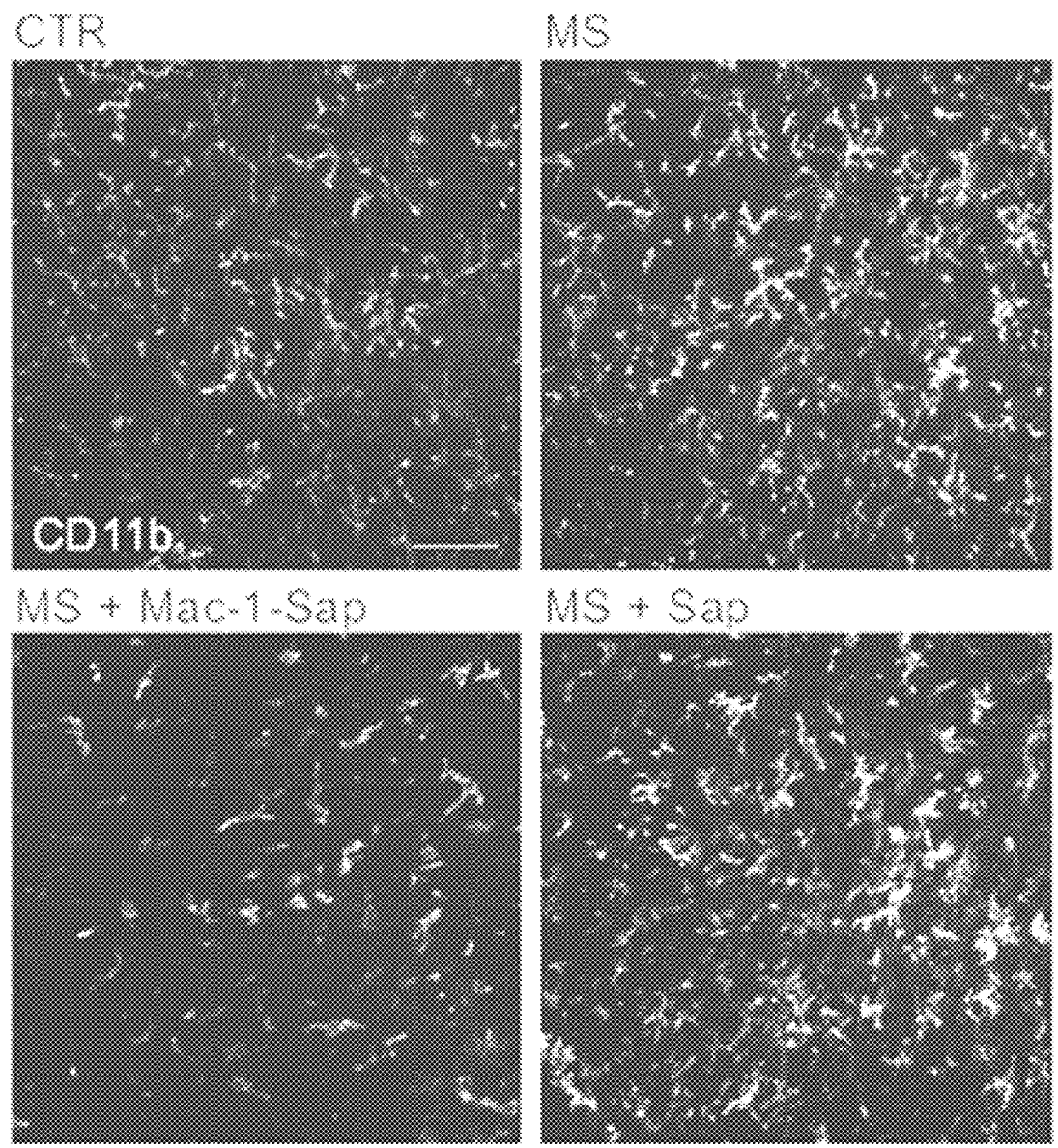
FIG. 4 is a series of micrograph images showing CD11b expression in rat spinal dorsal horn five days after morphine or saline treatment, and after microglial depletion with immunotoxin Mac1-saporin or unconjugated saporin (the scale bar represents 50 µm)
Figure 5:
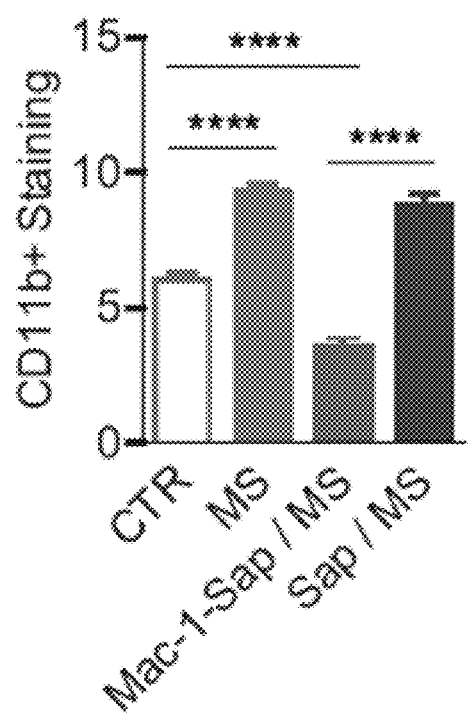
FIG. 5 is chart showing the effects of Mac1-saporin or unconjugated saporin on CD11b immunoreactivity in control rats and in morphine treated mice.
Figure 6:
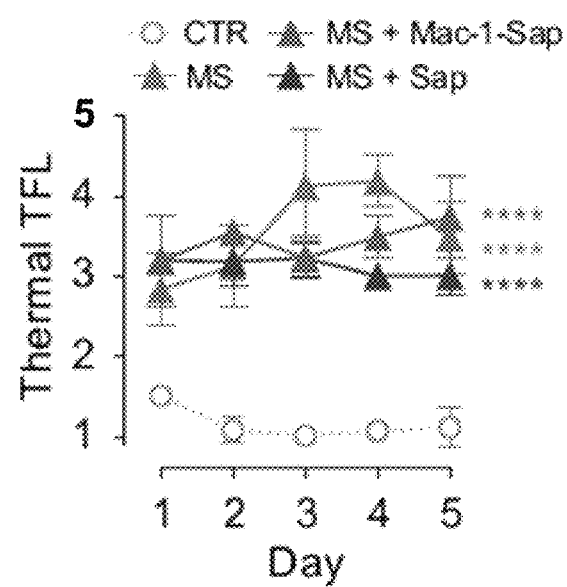
FIG. 6 is a chart showing morphine antinociception assessed with the thermal tail-flick test after morphine or control injections, or depletion of spinal microglia with Mac-1-saporin.

Morphine physical dependence was established in rats by administering systemic morphine sulfate twice daily over 5-days (FIG. 1). On day 5, injection of an opioid receptor antagonist naloxone (2 mg/kg, i.p.) precipitated a spectrum of withdrawal signs in morphine-treated rats; these signs were not observed when naloxone was administered to saline control rats (FIGS. 2, 3). Morphine administration increased CD11b-immunoreactivity in the spinal dorsal horn, indicating that spinal microglia respond to morphine treatment (FIGS. 4, 5). To test whether spinal microglia contribute to morphine withdrawal, microglia in the spinal cord of morphine-treated rats were depleted using intrathecal injections of a saporin-conjugated antibody to Mac1 (Mac1-saporin; 20 µg) (FIG. 1). Microglial depletion was localized to the spinal lumbar site of injection (FIGS. 4, 5), and did not alter the time-course or peak antinociceptive response to morphine (FIG. 6). Thus, morphine antinociception remained intact following Mac1-saporin treatment. By contrast, Mac1-saporin, but not unconjugated saporin control, significantly attenuated naloxone-precipitated withdrawal behaviours (FIG. 2). These results indicate that spinal microglia critically contribute to morphine withdrawal.

Figure 7:
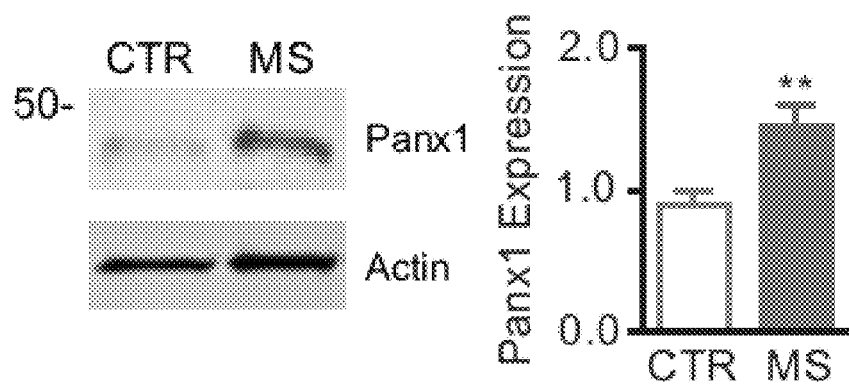
FIG. 7 shows a western blot and histogram comparing expression of local Panx1 protein in the lumbar spinal cords of morphine-withdrawn rats with control rats.
Figure 8:
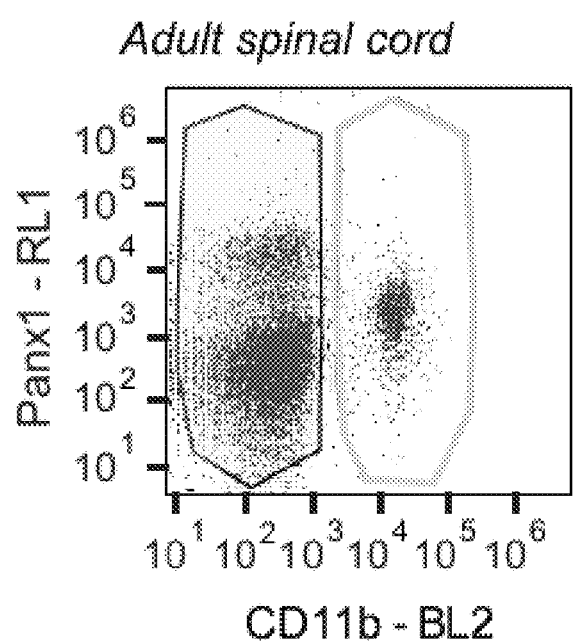
FIG. 8 is a histogram showing Panx1 expression in CD11b positive and CD11b negative populations using fluorescence-activated cell sorting.
Figure 9:
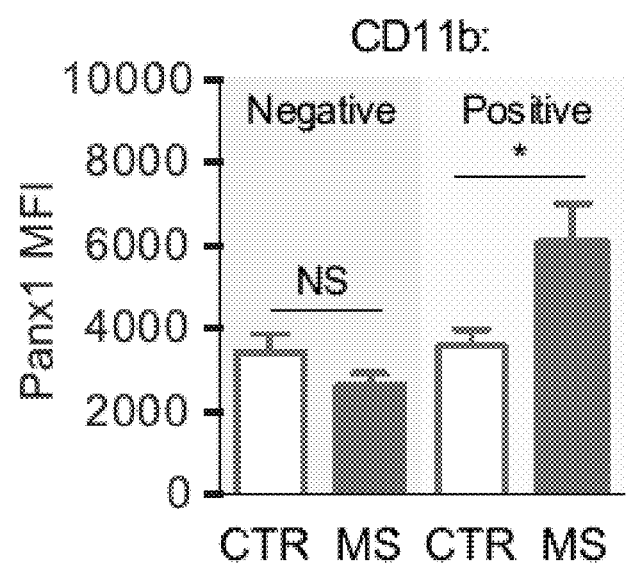
FIG. 9 is a chart showing the mean fluorescent intensity (MFI) of Panx1 staining in CD11b positive (MS) and CD11b negative populations (CTR) using fluorescence-activated cell sorting.
Figure 10:
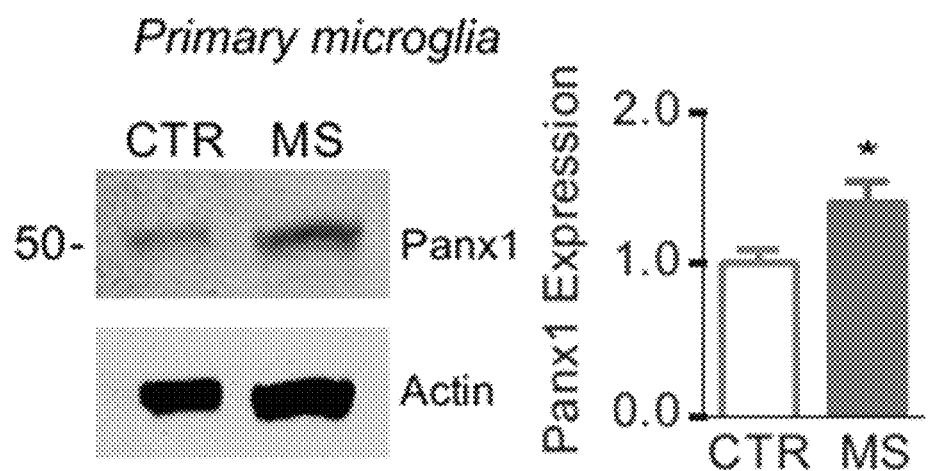
FIG. 10 shows a western blot and histogram of total Panx1 protein in primary microglia cultures following 5 days of morphine or saline (control) treatment.
Figure 11:
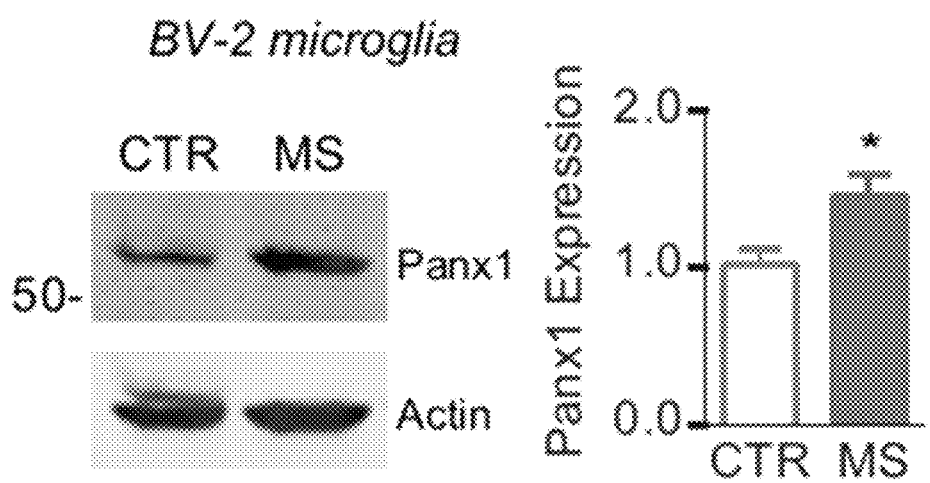
FIG. 11 shows a western blot and histogram of total Panx1 protein in immortalized BV-2 microglia cultures following 5 days of morphine or saline (control) treatment.
Figure 12:
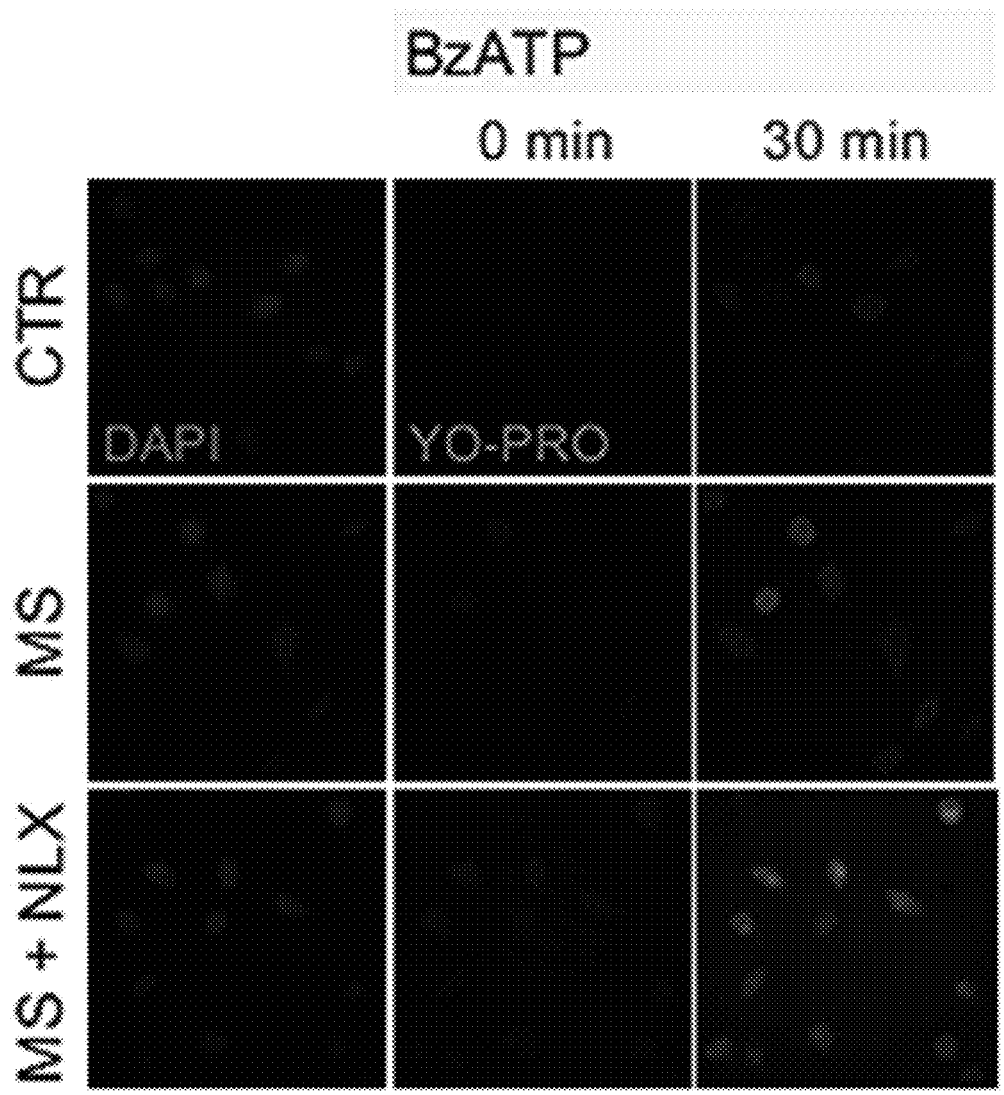
FIG. 12 shows representative images and/or traces of YO-PRO-1 dye-uptake in morphine, morphine/naloxone, and control treated BV-2 microglia after stimulation with BzATP (150 µM) for 30 min.
Figure 13:
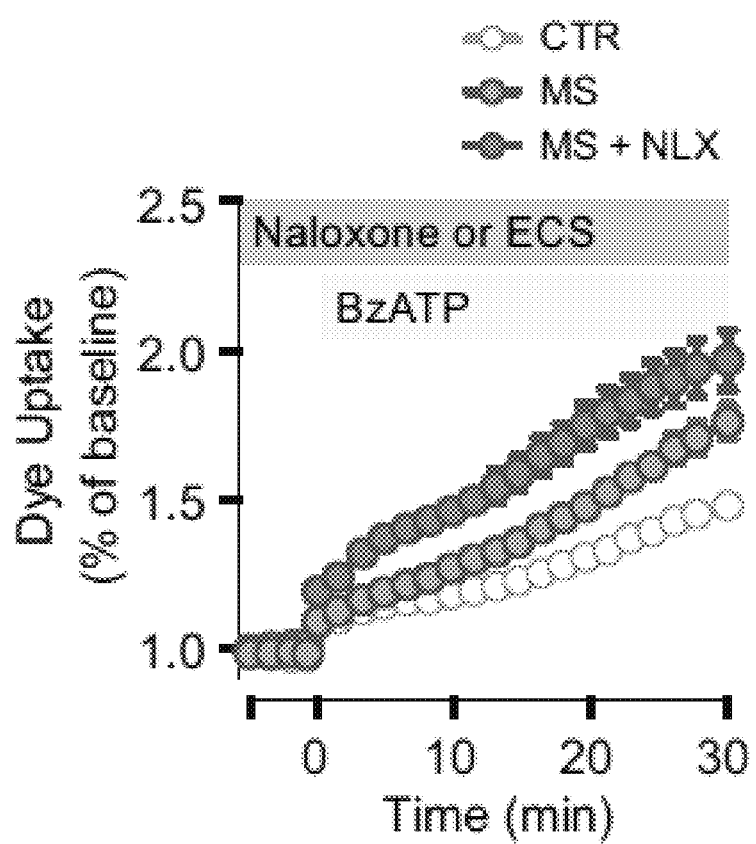
FIG. 13 is a chart showing representative traces of YO-PRO-1 dye-uptake in BV-2 microglia treated with morphine or saline, and microglia pre-treated with naloxone (10 µM) on potentiated total dye-uptake in morphine treated microglia at 30 minutes compared to microglia treated with morphine alone and to saline-treated microglia.
Figure 14:
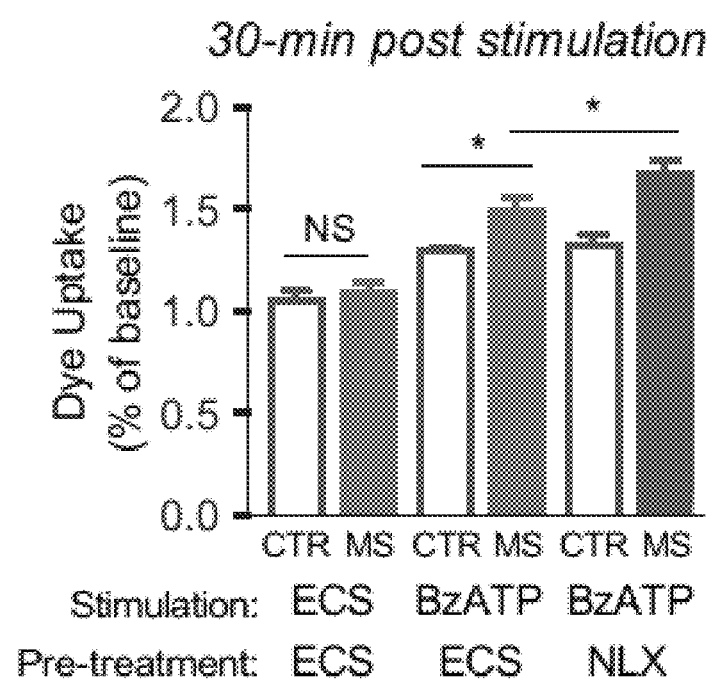
FIG. 14 is a histogram showing the effects of pre-treatment with naloxone (10 µM) for 10 min or inactive peptide $^{sc}$panx (10 µM) on BzATP-evoked dye-uptake.
Figure 15:
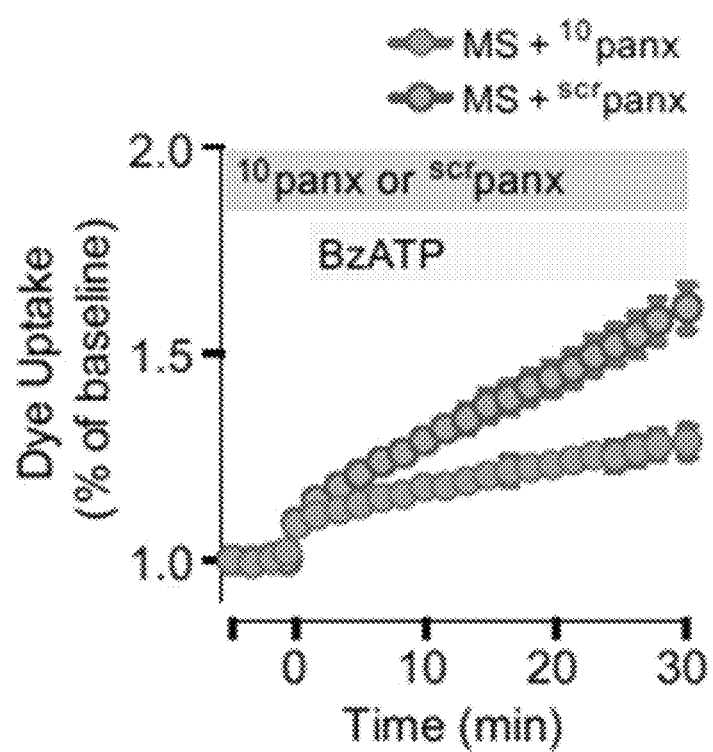
FIG. 15 is a chart showing the effects of treatment with the Panx1 blocker $^{10}$panx (10 µM) on potentiated total dye-uptake in morphine treated microglia at 30 minutes compared to saline-treated microglia or microglia stimulated with ECS.
Figure 16:
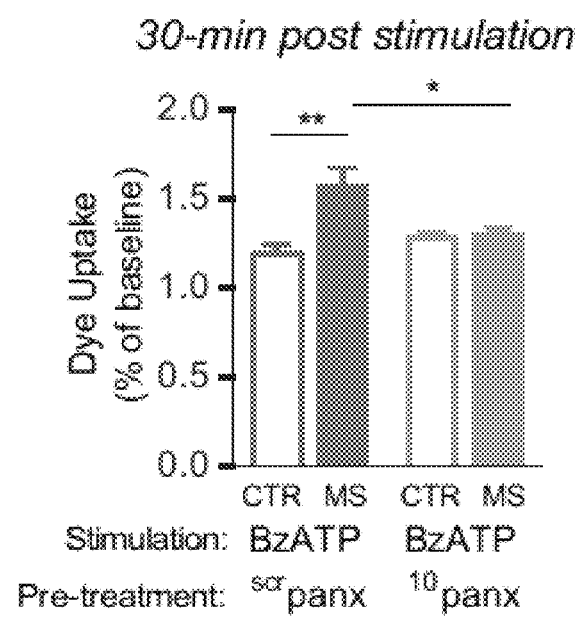
FIG. 16 is a chart showing the effects of pretreatment with the Panx1 blocker $^{10}$panx (10 µM) followed by stimulation with BzATP (150 µM) for 30 min on potentiated total dye-uptake in morphine treated microglia at 30 minutes compared to saline-treated microglia or microglia stimulated with ECS.
Figure 17:
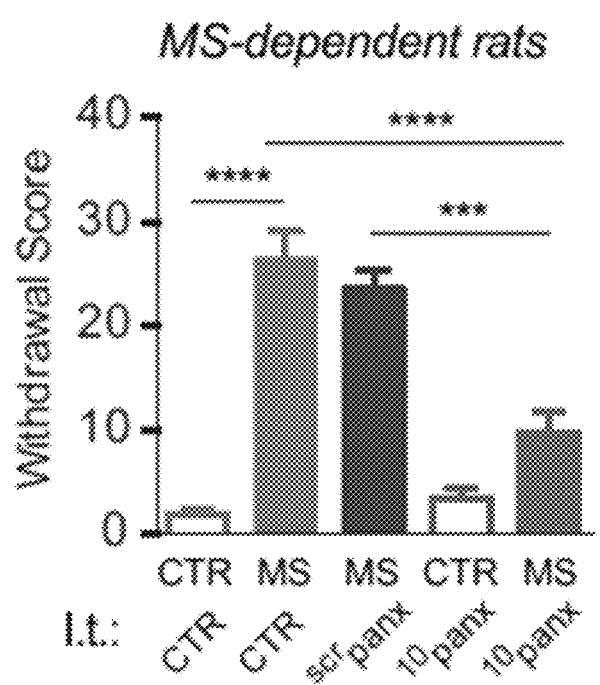
FIG. 17 is a chart showing the effects of intrathecal Panx1 blocker $^{10}$panx on behavioural signs of morphine withdrawal.

In the spinal cord, Panx1 protein expression was significantly greater in morphine as compared with saline-treated rats (FIG. 7). Flow cytometric analysis indicated that the morphine-induced increase occurred in CD11b-positive cells (FIGS. 8, 9), suggesting that the increased Panx1 expression was microglia specific. To determine whether morphine acts directly on microglia to modulate Panx1 expression, rat primary microglia cultures and a BV-2 microglial cell line were treated with morphine for 5-days, and found in both cell culture systems a marked increase in total Panx1 protein levels (FIG. 10, 11). The effects of morphine treatments on Panx1 activity were assessed by measuring BzATP-evoked uptake of YO-PRO-1, a large molecular weight dye. BzATP (150 µM) caused a significantly greater uptake of YO-PRO-1 in morphine as compared with saline-treated microglia (FIGS. 12, 13, 14). In morphine-treated cells, YO-PRO-1 uptake was further potentiated in the presence of naloxone (10 µM) (FIGS. 12, 13, 14) and blocked by the small peptide Panx1 inhibitor $^{10}$panx (10 µM), but unaffected by the scrambled peptide $^{scr}$panx (FIGS. 15, 16). Thus, it was determined that morphine treatment upregulates the expression and activity of Panx1 autonomously in microglia.

Figure 18:
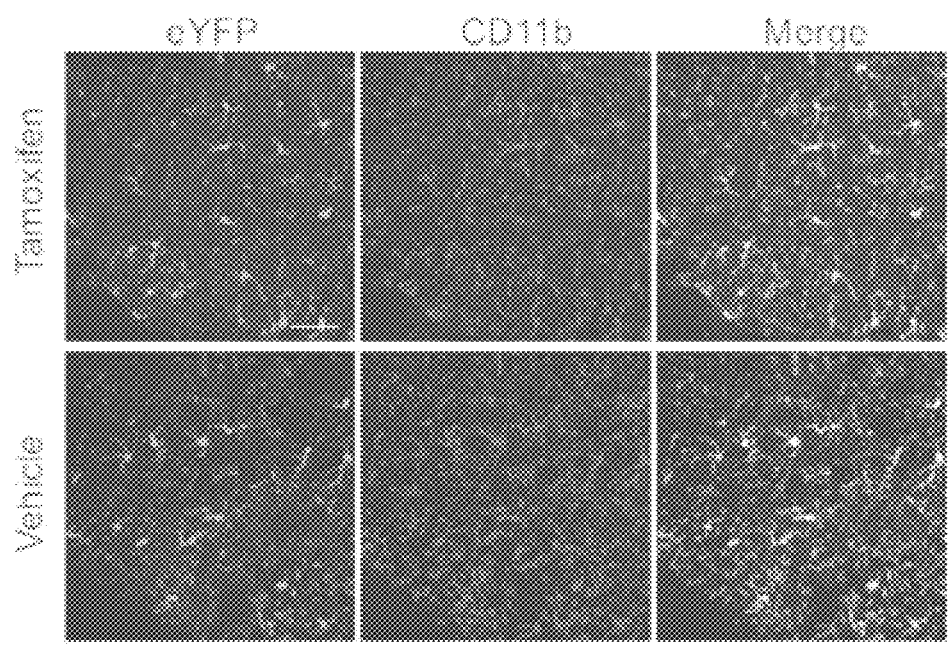
FIG. 18 is a series of micrograph images showing expression of Cre reporter eYFP and CD11b in spinal dorsal horn of tamoxifen and vehicle treated Cx3cr1::Panx1$^{flx/flx}$ mice.
Figure 19:
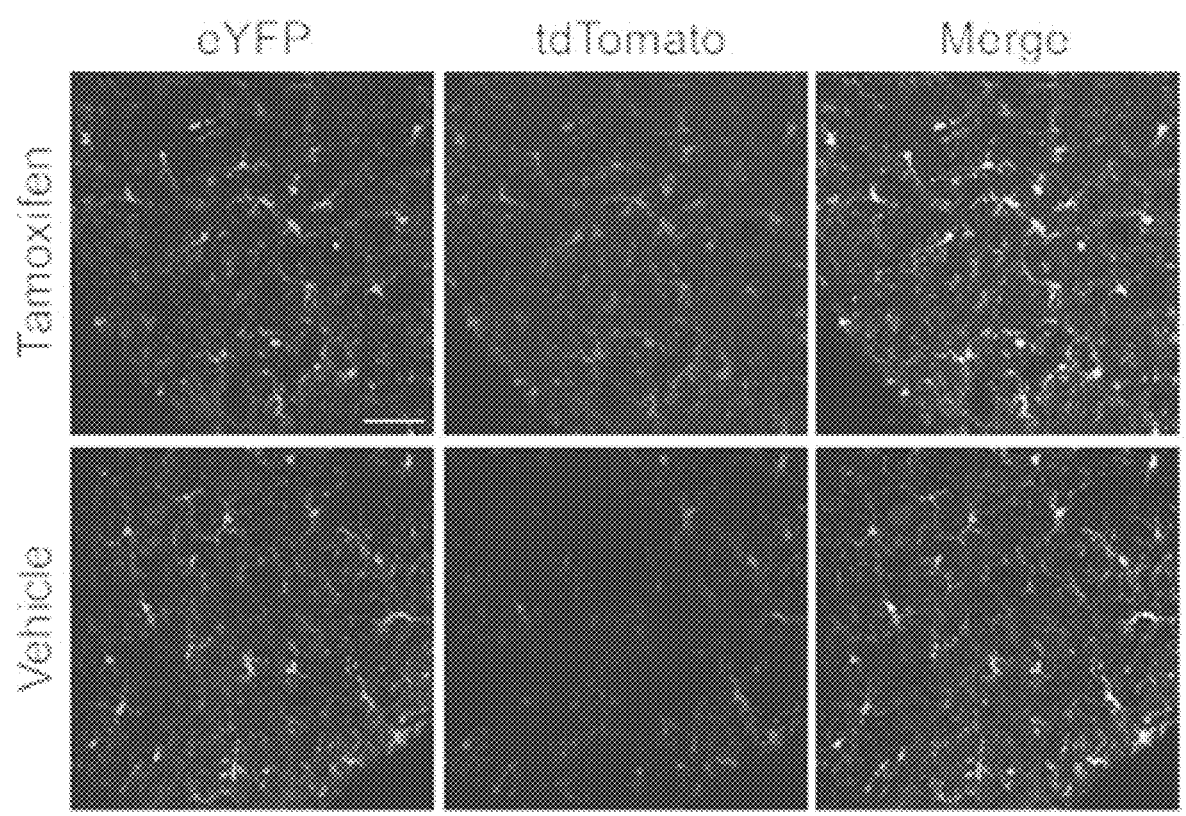
FIG. 19 is a series of micrograph images showing expression of Cre reporter eYFP and CD11b in spinal dorsal horn of control mice and in morphine treated mice.
Figure 20:
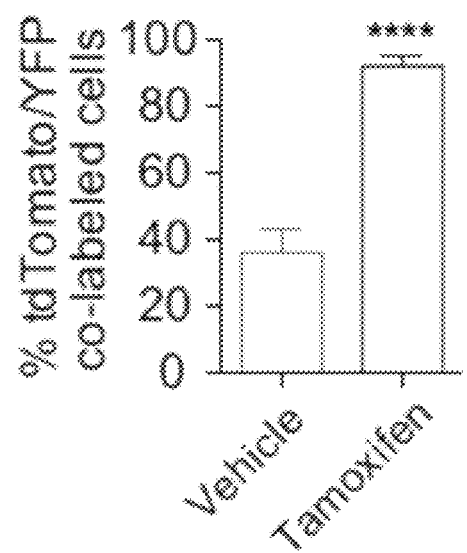
FIG. 20 is a chart showing % co-labeled eYFP and tdTomato cells in Ai14-tdTdmato-reporter mice following 5 days of tamoxifen or vehicle administration.
Figure 21:
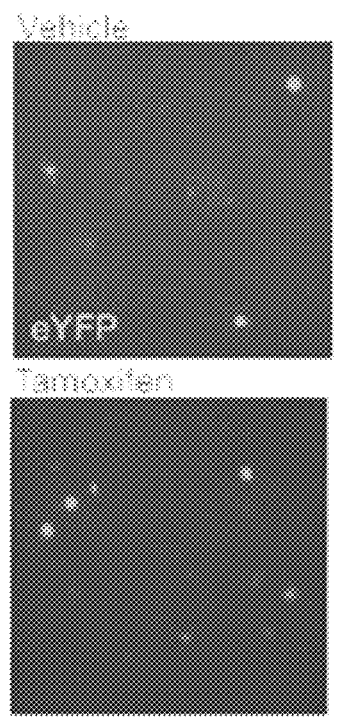
FIG. 21 are micrograph images of eYFP positive microglia isolated from adult Cx3cr1::Panx1$^{flx/flx}$ mice.
Figure 22:
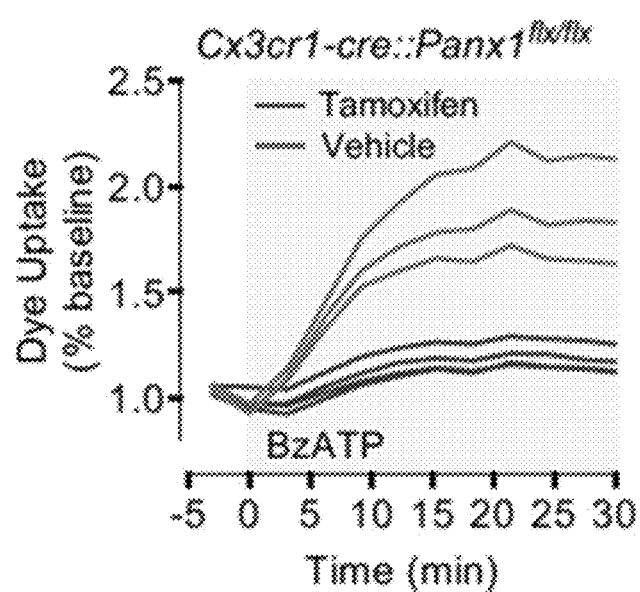
FIG. 22 is a chart showing BzATP-evoked YO-PRO-3 dye uptake in microglia isolated from adult Cx3cr1::Panx1$^{flx/flx}$ mice pre-treated with tamoxifen or vehicle.
Figure 23:
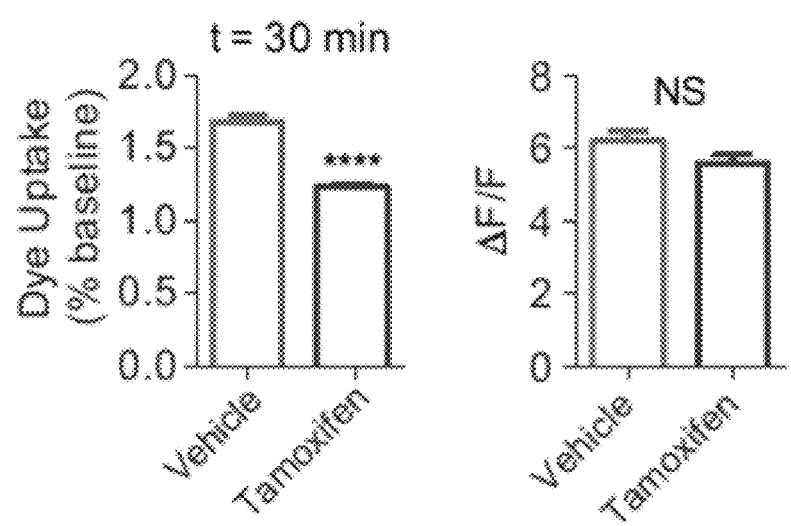
FIG. 23 is a chart showing the effects of tamoxifen on uptake of calcium indicator dye ura-2AM in morphine treated mice and control mice.
Figure 24:
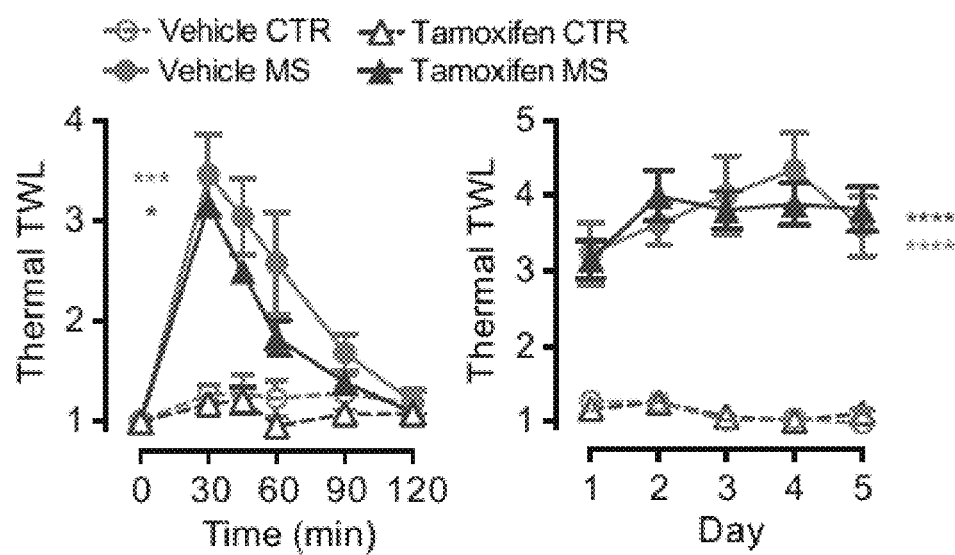
FIG. 24 are charts showing the effects morphine-induced antinociception in Cx3cr1::Panx1$^{flx/flx}$ mice using the thermal tail emersion test.
Figure 25:
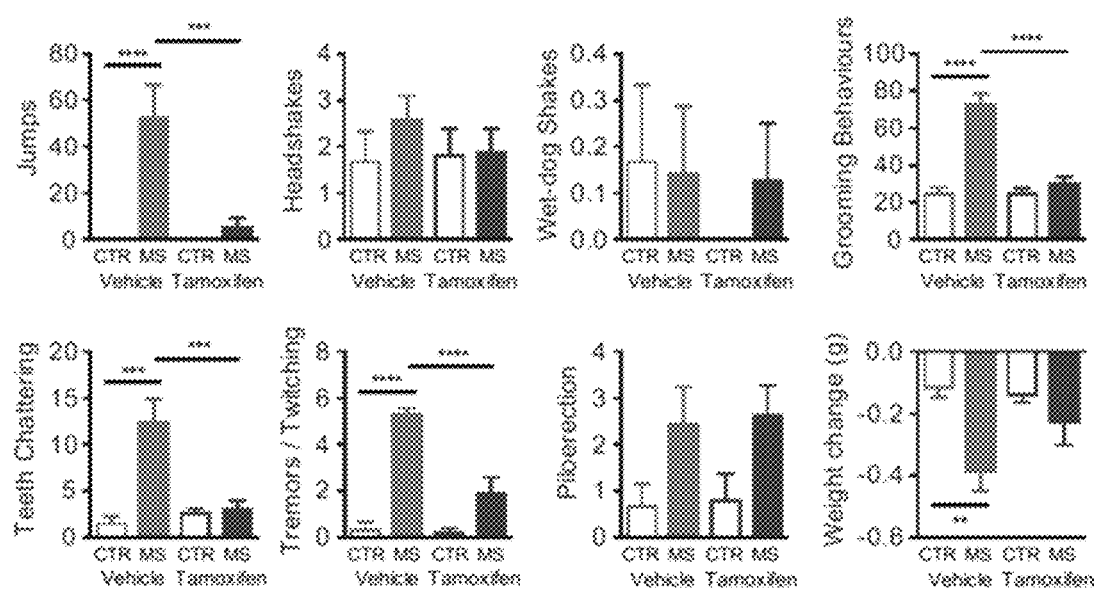
FIG. 25 shows charts of individual autonomic and somatic withdrawal behaviors in morphine treated mice and control mice.
Figure 26:
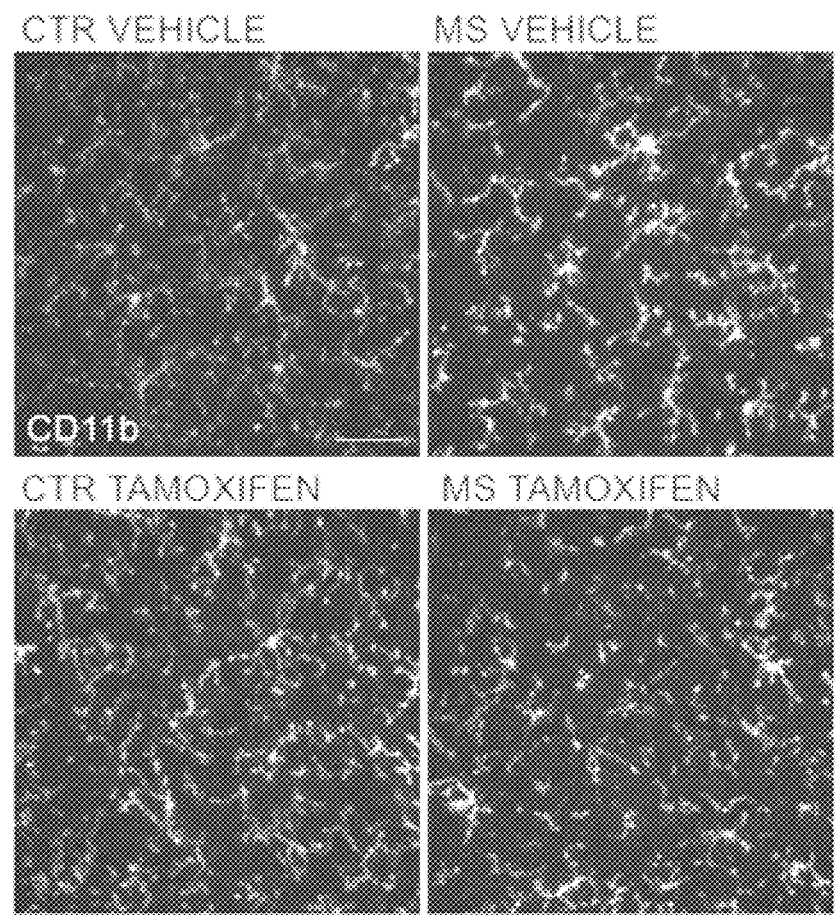
FIG. 26 shows micrograph images of the effects of tamoxifen on CD11b expression in spinal dorsal horns of morphine treated and control Cx3cr1::Panx1$^{flx/flx}$ mice.
Figure 27:
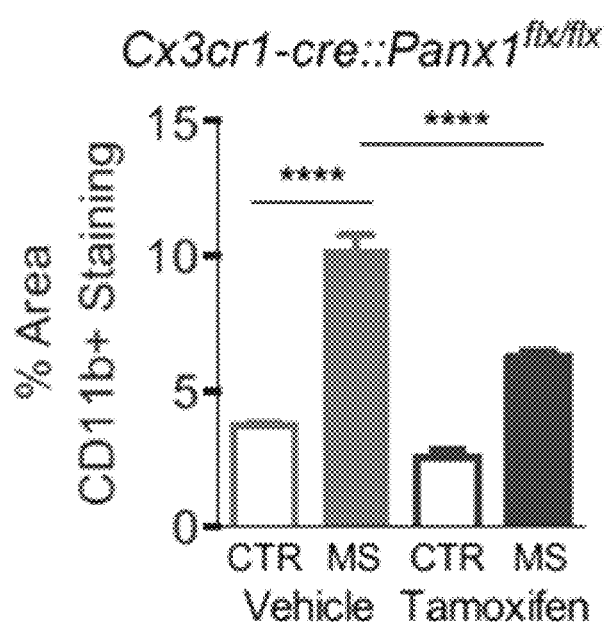
FIG. 27 is a chart showing the percent area of CD11b expression in the spinal dorsal horn of morphine treated mice and control Cx3cr1::Panx1$^{flx/flx}$ mice.
Figure 28:
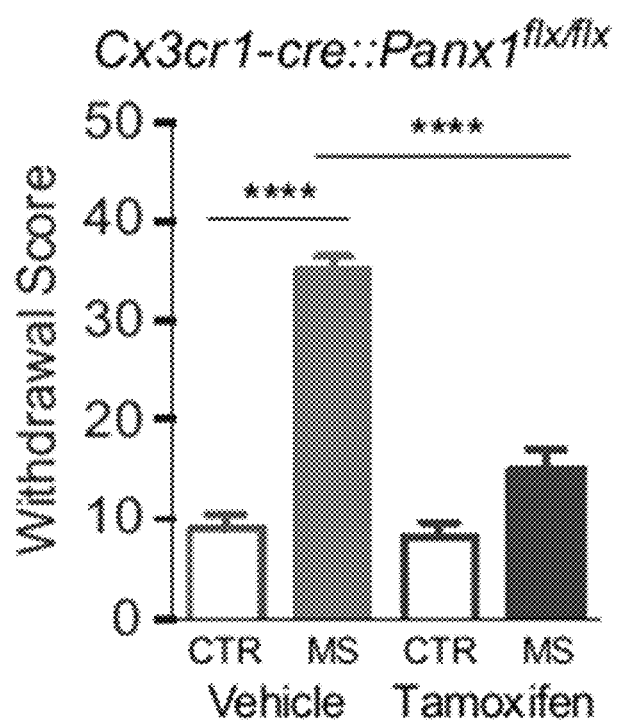
FIG. 28 is a chart showing naloxone-precipitated withdrawal in tamoxifen and vehicle treated Cx3cr1-cre::Panx1$^{flx/flx}$ mice (mutant mice generated with a targeted deletion of Panx1 from microglial cells ie. mice with a tamoxifen-inducible deletion of Panx1 from Cx3cr1-expressing cells)

The observation that naloxone potentiates Panx1 activity in morphine-treated microglia suggested that Panx1 might contribute to naloxone-induced morphine withdrawal behaviours. This was tested by intrathecally administering $^{10}$panx (10 µg) in rats with established physical dependence after 5-days of morphine treatment. $^{10}$panx administration 60-minutes prior to naloxone challenge significantly attenuated withdrawal behaviours, indicating the requisite Panx1 is expressed on microglia. Transgenic mice were generated with a tamoxifen-inducible deletion of Panx1 in $CX_3CR_1$-expressing cells (Cx3cr1-cre::Panx1$^{flx/flx}$). These transgenic mice were used to confirm that the Cre$^{ER}$ reporter eYFP was localized to CD11b-positive cells in the lumbar spinal cords (FIG. 18), and that 7-days after tamoxifen treatment there was recombination in 95±3.1% of these cells (FIGS. 19, 20). Moreover, spinal microglia isolated from adult mice lacking Panx1 (tamoxifen-injected Cx3cr1-cre::Panx1$^{flx/flx}$) showed significant impairment in YO-PRO uptake (FIGS. 21, 22), but possessed normal P2X7R cation channel activity (FIG. 23). Although these mutant mice retained normal antinociceptive responses to morphine (FIGS. 24, 25), spinal microglial reactivity to morphine was blunted (FIGS. 26, 27), and when challenged with naloxone they displayed significantly less withdrawal behaviors than morphine-treated mice that express the full complement of Panx1 channels (littermate vehicle-injected Cx3cr1-cre::Panx1$^{flx/flx}$ mice) (FIG. 28).

Figure 29:
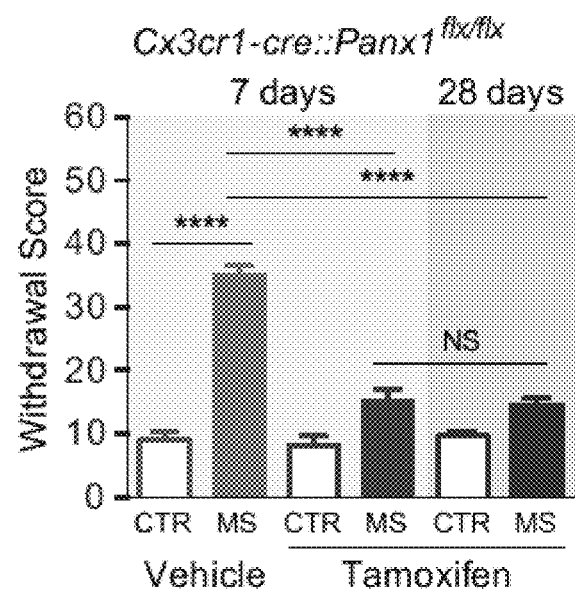
FIG. 29 is a chart illustrating that microglial Panx1 (rather than peripheral Cx3cr1-expressing cells) are directly involved during morphine withdrawal.
Figure 30:
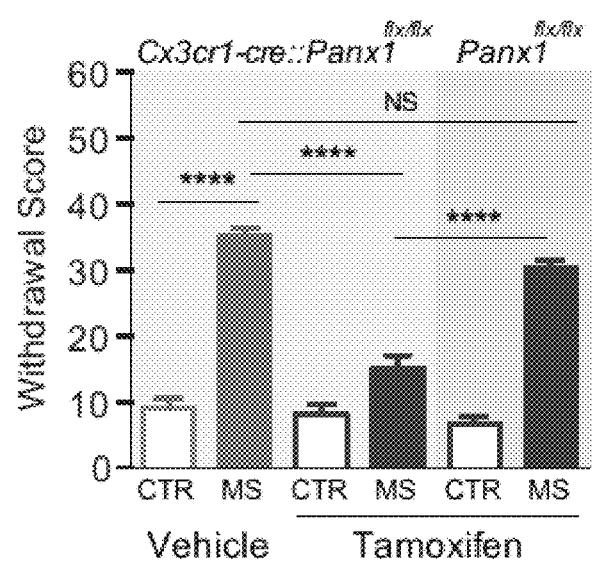
FIG. 30 is a chart showing the withdrawal scores from Cx3cr1::Panx1$^{flx/flx}$ mice and Pnx1$^{flx/flx}$ mice that received 5 days of tamoxifen treatment prior to morphine administration.
Figure 31:
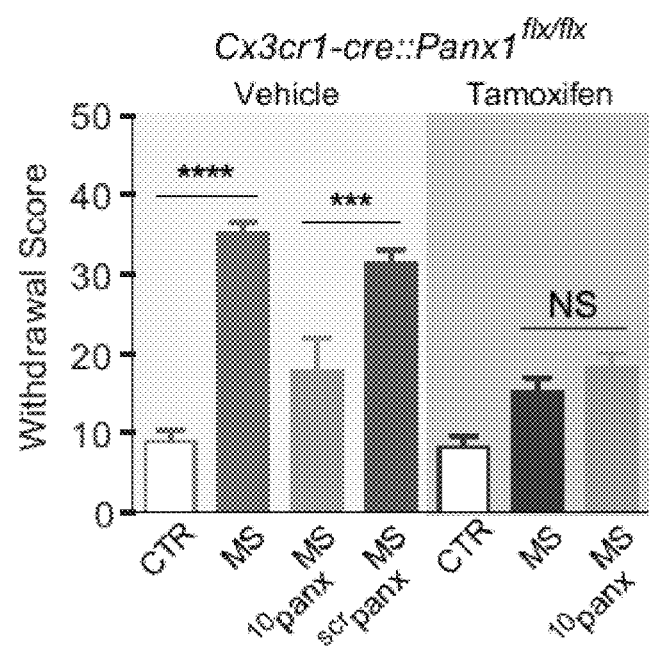
FIG. 31 is a chart showing the effects of acute intrathecal injection of Panx1 blocker $^{10}$panx into morphine-dependent tamoxifen and vehicle treated Cx3cr1::Panx1$^{flx/flx}$ mice 1 hour prior to naloxone-precipitated withdrawal.

Given that cell turnover rates differ between central and peripheral $CX_3CR_1$-expressing populations (Parkhurst et al., 2013), another cohort of mice was given a 30-day waiting period after tamoxifen treatment to allow for repopulation of peripheral CX₃CR₁-expressing cells before initiating morphine treatment. These mice therefore lacked Panx1 only in microglia. The reduction in morphine withdrawal in this cohort of mice was comparable to mice treated with morphine 7-days post-tamoxifen treatment (FIG. 29), indicating that Panx1 expressed specifically on microglia is required for morphine withdrawal. As another control, tamoxifen was administered to Panx1$^{loxp/loxp}$ mice which do not have inducible Cre-recombinase, and their morphine withdrawal responses were indistinguishable from those displayed by Panx1-expressing mice (FIG. 30). Thus, tamoxifen per se does not affect morphine withdrawal. To further investigate the requirement for microglial Panx1, the effects of intrathecal $^{10}$panx (10 µg) treatments on naloxone-precipitated morphine withdrawal in Panx1-deficient versus Panx1-expressing mice were assessed. The rationale was that if the effects of $^{10}$panx were mediated by blocking Panx1 activity on microglia, then these effects would be lost in the absence of microglial Panx1. Consistent with the data collected with rats, intrathecal $^{10}$panx treatment before naloxone challenge significantly attenuated morphine withdrawal in Panx1-expressing mice (FIG. 31). By contrast, in mice lacking microglial Panx1 and that have suppressed morphine withdrawal behaviors, $^{10}$panx did not further reduce withdrawal (FIG. 31). The loss of $^{10}$panx effect together with the amelioration of withdrawal in Panx1-deficient mice, critically implicate microglial Panx1 in morphine withdrawal.

Figure 32:
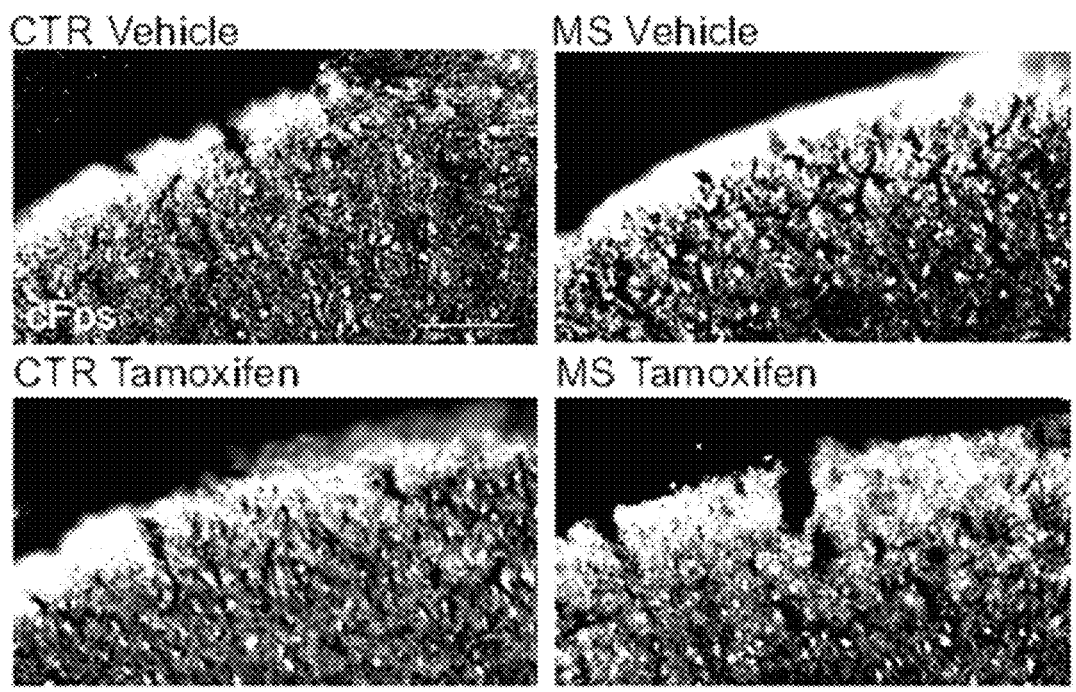
FIG. 32 shows micrograph images of cFos expression in the spinal dorsal horns of vehicle and tamoxifen treated Cx3cr1::Panx1$^{flx/flx}$ mice following five days of morphine or saline treatment.
Figure 33:
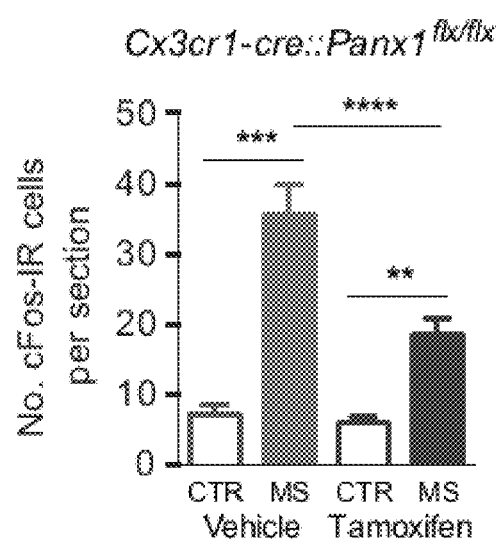
FIG. 33 is a chart showing the distribution of cFos immunoreactive neurons in superficial lamina of spinal cord from tamoxifen and vehicle treated Cx3cr1::Panx1$^{flx/flx}$ mice following five days of morphine or saline treatment.
Figure 34:
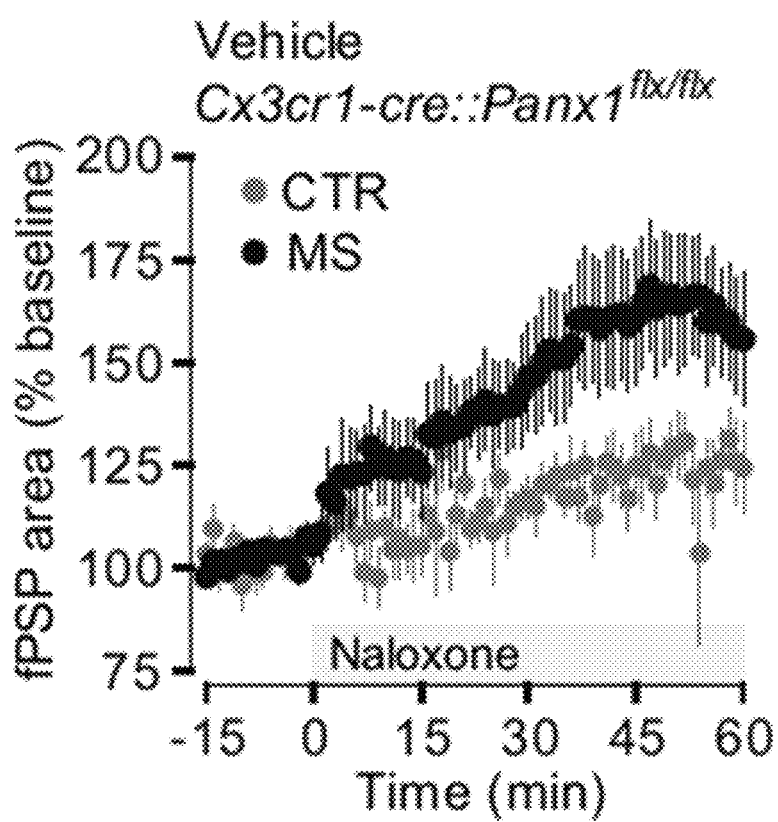
FIG. 34 is a chart showing facilitation of field postsynaptic potentials (fPSPs) induced by naloxone application (10 μM) in spinal dorsal horn (SDH) of morphine-treated and control treated Cx3cr1::Panx1$^{flx/flx}$ vehicle mice.
Figure 35:
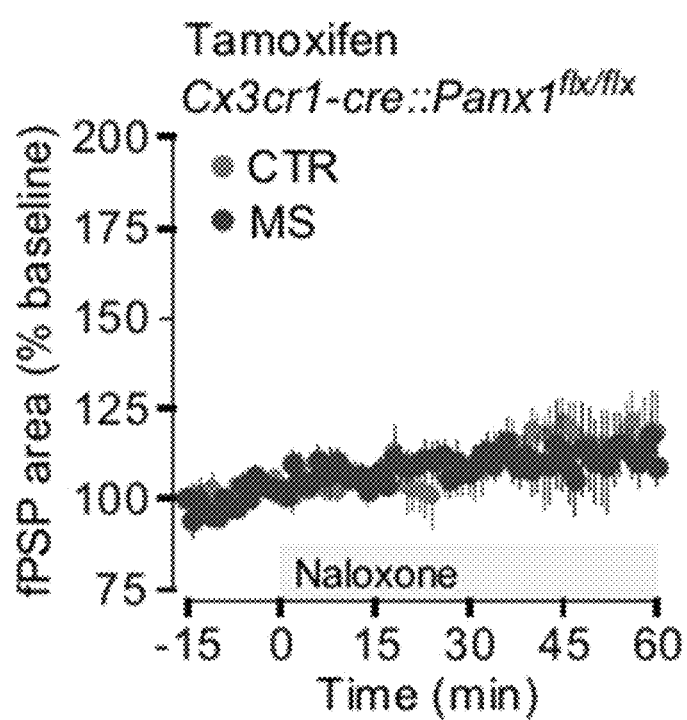
FIG. 35 is a chart showing that naloxone does not cause facilitation of SDH neurons in morphine-treated mutant mice.
Figure 36:
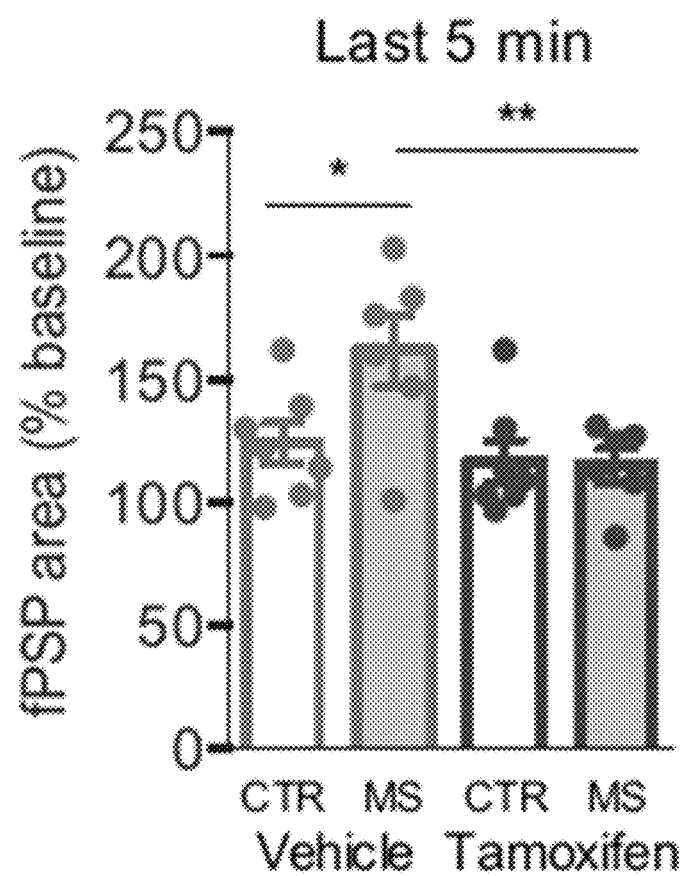
FIG. 36 is a chart showing average fPSP areas during the last 5 min of SDH recordings in morphine-treated and in tamoxifen Cx3cr1::Panx1$^{flx/flx}$ mice.
Figure 37:
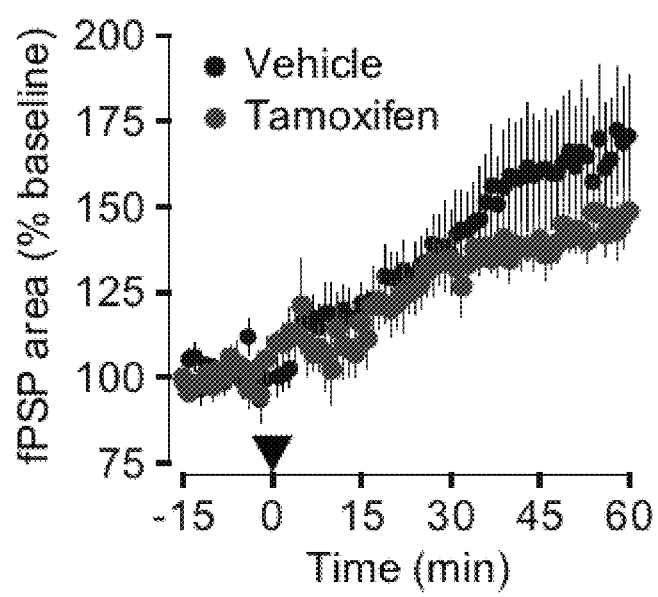
FIG. 37 is a chart showing facilitation of fPSPs in lamina I/II of tamoxifen and vehicle treated Cx3cr1::Panx1$^{flx/flx}$ mice following low frequency (2 Hz) electrical stimulation of dorsal roots (black arrow)
Figure 38:
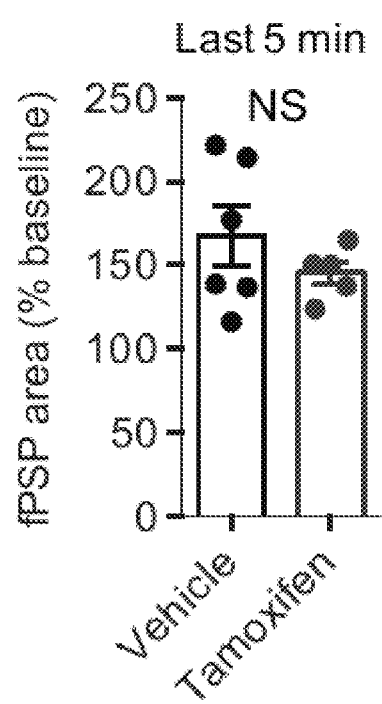
FIG. 38 is a chart showing the average fPSP areas over last 5-min of electrical facilitation experiments in tamoxifen and vehicle-treated Cx3cr1::Panx1$^{flx/flx}$ mice.

To investigate the mechanism underlying Panx1-mediated withdrawal, c-Fos expression was measured and indicated that naloxone-precipitated withdrawal increased the number of c-Fos-positive neurons within the spinal dorsal horn of Panx1-expressing mice, This increase was suppressed in mice lacking microglial Panx1 (FIGS. 32, 33). A whole lumbar spinal cord preparation with intact dorsal roots prepared from Panx1-expressing or microglial Panx1-deficient adult mice that received either 5-day saline or morphine injections was used to directly assess neuronal function. Postsynaptic field potentials (fPSPs) from lamina-I/II of the spinal dorsal horn were recorded and it was noted that bath applications of naloxone (10 µM) produced a slow-rising synaptic facilitation that persisted for at least 60 min in morphine, but not saline-treated, Panx1-expressing mice (FIGS. 34, 36). By contrast, this response to naloxone did not occur in morphine-treated Panx1-deficient mice (FIGS. 35, 36). The absence of synaptic facilitation in these mutant mice was not due to a general defect in spinal synaptic facilitation because electrically stimulating the dorsal roots at low frequency (2 Hz) produced a robust and long-lasting increase in fPSPs (FIGS. 37, 38). These data suggest that morphine induces plasticity in the spinal dorsal horn, which may manifest as long-term synaptic facilitation upon naloxone-induced withdrawal. This synaptic facilitation appears to require microglial Panx1 activation in a manner similar to morphine withdrawal.

Figure 39:
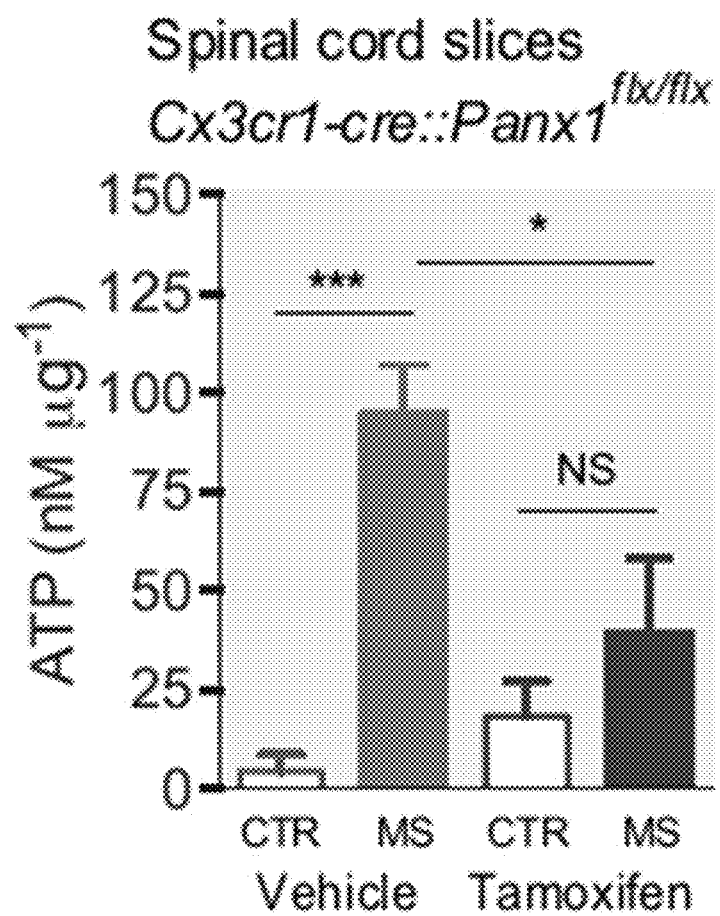
FIG. 39 is a chart showing naloxone-stimulated ATP levels in ACSF superfusates from lumbar spinal cord slices taken from morphine-treated or control mutant mice.
Figure 40:
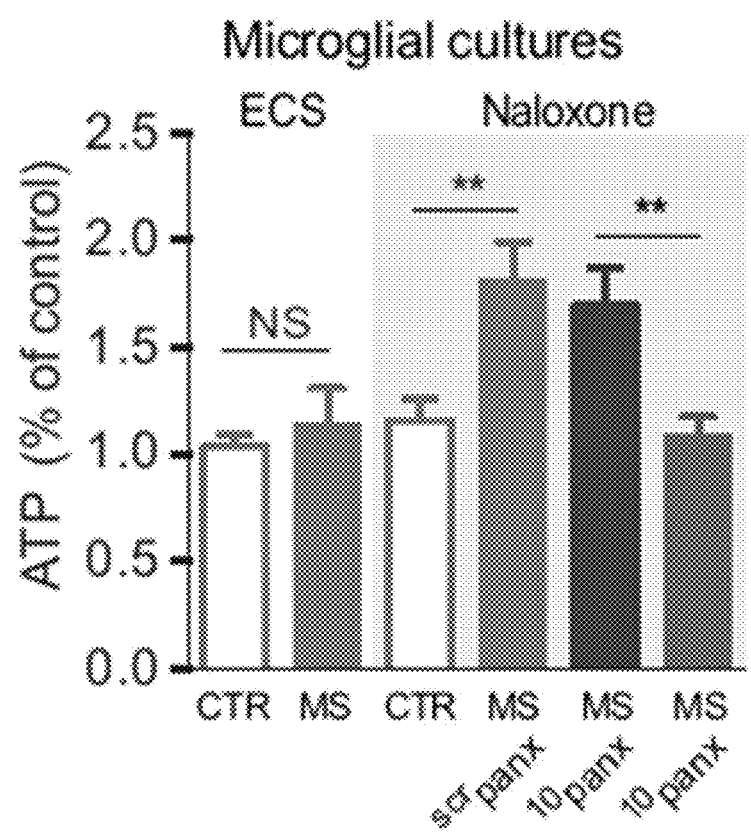
FIG. 40 is a chart showing ATP levels in supernatants collected from naloxone or ECS-stimulated cultured microglia following 5 days of morphine or saline treatment.

Since ATP release is a key consequence of Panx1 activation, the question was raised whether or not Panx1-mediated ATP release occurs during withdrawal. To test this, naloxone (10 µM) was bath-applied to/spinal cord slices isolated from Panx1-expressing and Panx1-deficient mice that were treated with 5-day saline or morphine. The amounts of ATP in spinal superfusates were measured and it was found that the level of ATP in response to naloxone was significantly greater in morphine versus saline-treated Panx1-expressing mice. This naloxone-induced effect was not observed in slices prepared from Panx1-deficient mice (FIG. 39). To separately test whether ATP is released from microglia, naloxone was applied to microglia in culture and measured the amount of ATP in the microglial supernatant. Naloxone evoked the release of ATP, which was blocked by $^{10}$panx (FIG. 40).

Figure 41:
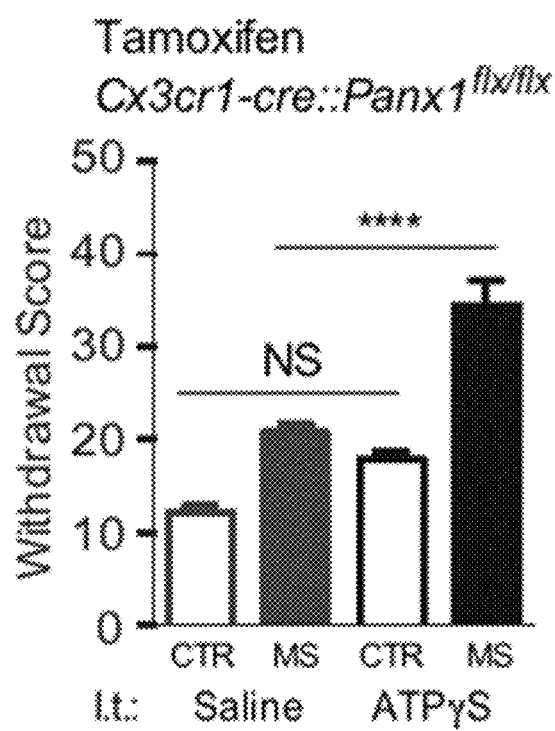
FIG. 41 is a chart showing the effects of an acute intrathecal injection of ATPγS (100 μM, given immediately prior to naloxone) in morphine-dependent and control mutant mice.
Figure 42:
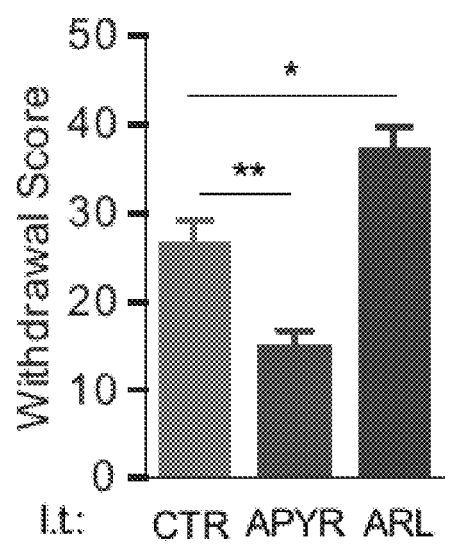
FIG. 42 is a chart showing the effects of Intrathecal injections of the apyrase (ATPase, 10 units, 15-min prior to naloxone) and ARL67156 (ATPase inhibitor, 10 nmoles, 15-min prior to naloxone) attenuated withdrawal symptoms in morphine-dependent rats.

To directly test whether ATP contributes to morphine withdrawal, ATPγS was administered intrathecally to Panx1-deficient mice that display attenuated morphine withdrawal behaviors. In these mutant mice, local delivery of the ATP analogue (100 µM), together with naloxone challenge, restored a spectrum of withdrawal behaviors; these behaviors were not observed when ATPγS was administered to saline-treated Panx1-deficient mice (FIG. 41). It was reasoned that if ATP is a critical substrate of morphine withdrawal, then altering endogenous ATP levels in the spinal cord might affect withdrawal behaviors. This possibility was tested in morphine-dependent Panx1-expressing mice by intrathecal injection of an ATP-degrading enzyme apyrase (10 units), which produced a striking reduction in withdrawal (FIG. 42). Conversely, inhibiting ATP breakdown by intrathecally administering an ecto-ATPase inhibitor ARL67156 (10 nmoles) exacerbated morphine withdrawal (FIG. 42). Therefore, the conclusion is that ATP is a critical substrate for morphine withdrawal.

Figure 43:
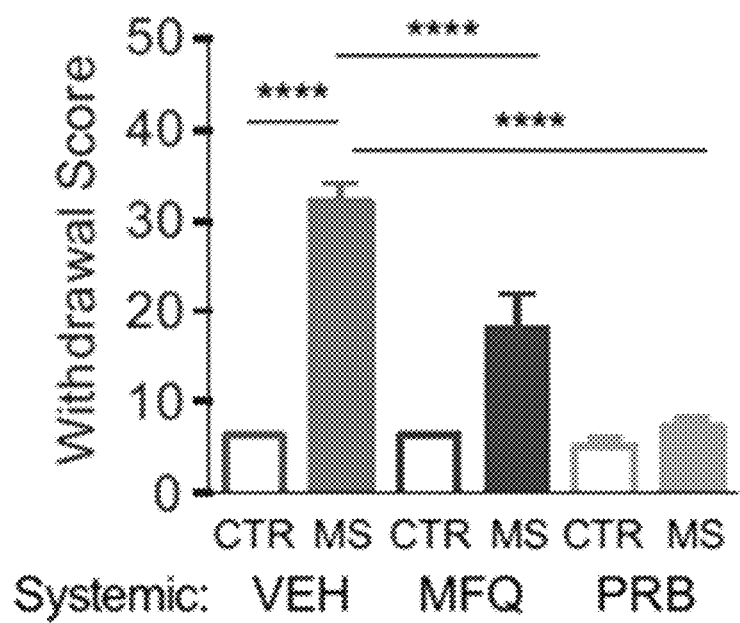
FIG. 43 is a chart showing the effects of systemic administration of mefloquine (MFQ) or probenecid (PRB) on withdrawal behaviours in morphine treated and control rats.
Figure 44:
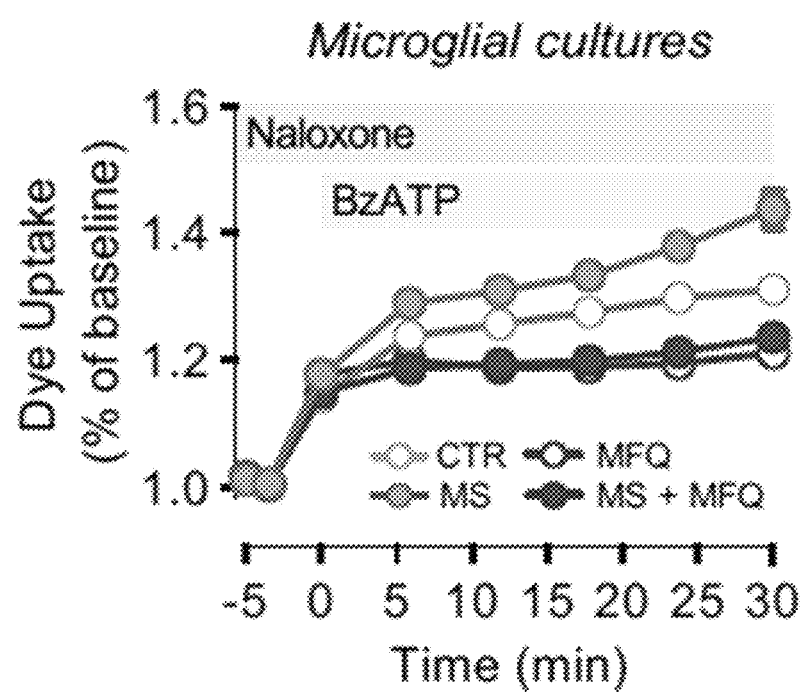
FIG. 44 is a chart showing the effects of mefloquine on YO-PRO-3 dye uptake in BV-2 microglial cultures.
Figure 45:
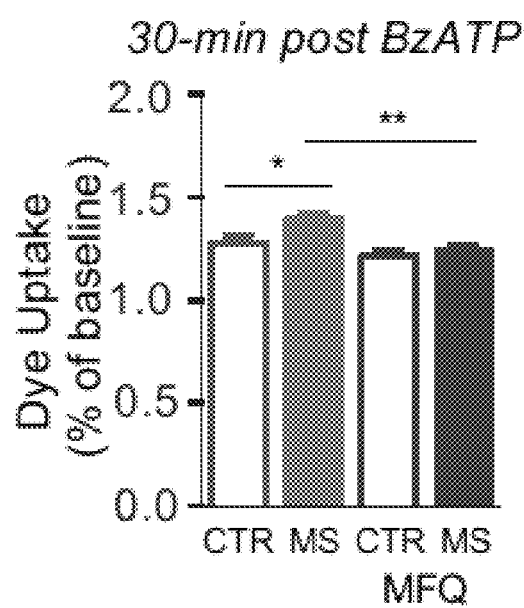
FIG. 45 is a chart showing the effects of mefloquine on YO-PRO-3 dye uptake at 30 minutes post-BzATP in BV-2 microglial cultures.
Figure 46:
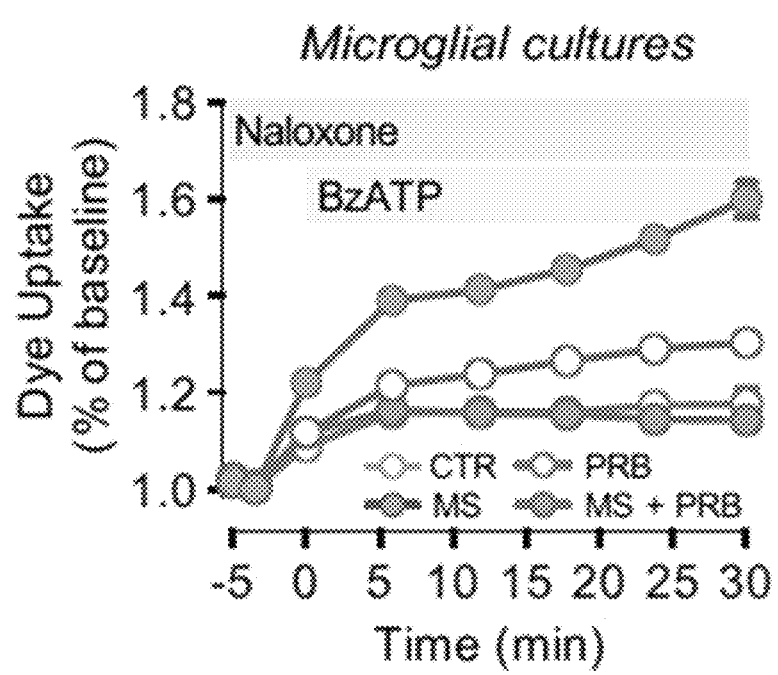
FIG. 46 is a chart showing the effects of probenecid on YO-PRO-3 dye uptake in BV-2 microglial cultures.
Figure 47:
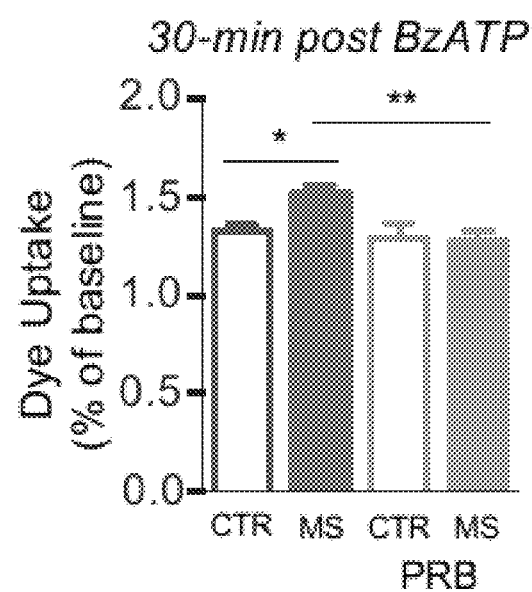
FIG. 47 is a chart showing the effects of probenecid on YO-PRO-3 dye uptake at 30 minutes post-BzATP in BV-2 microglial cultures.
Figure 48:
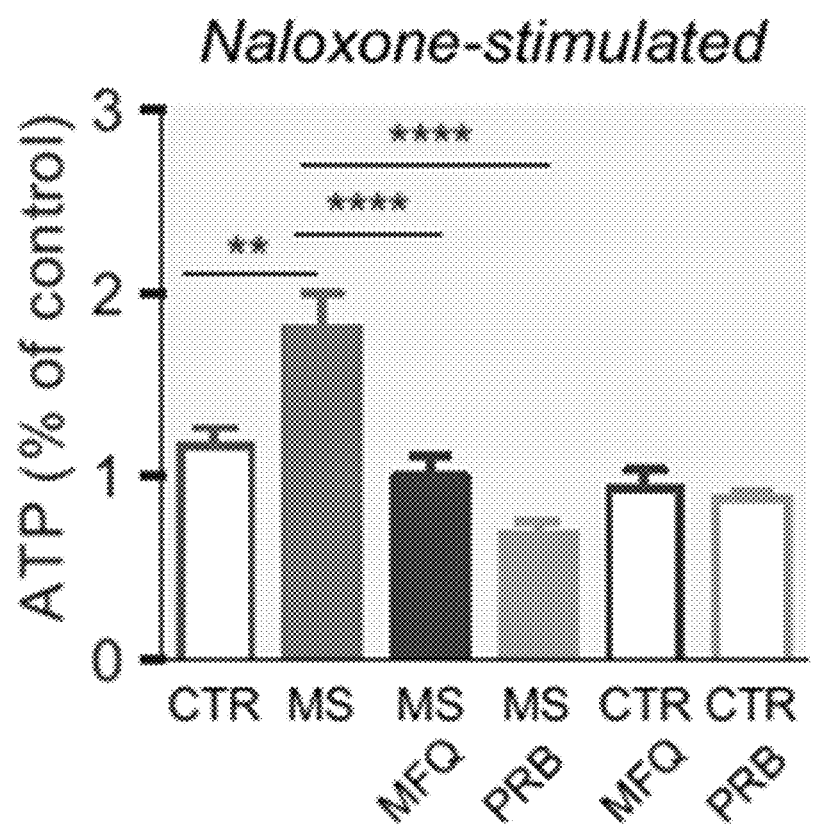
FIG. 48 is a chart showing the effects of mefloquine and probenecid on ATP levels collected from cultured microglia stimulated with naloxone.

Having established that Panx1 is critically involved in morphine withdrawal, two clinically approved broad-spectrum Panx1 inhibitors, probenecid, an anti-gout medication, and mefloquine, an anti-malarial drug, were tested to assess their effects on morphine withdrawal. In morphine-dependent rats, systemic administration of probenecid (50 mg/kg) or mefloquine (45 mg/kg) 1-hour prior to naloxone challenge significantly ameliorated morphine withdrawal (FIG. 43). These compounds also blocked naloxone potentiation of Panx1 activation and suppressed ATP release in morphine-treated cultured microglia (FIGS. 44, 45, 46, 47, 48). The robust effects of probenecid and mefloquine on morphine withdrawal open the possibility that these, and other clinically available broad-spectrum Panx1 inhibitors, could be translated into the treatment of opiate withdrawal.

In summary, withdrawal is a major deterrent for cessation of opiate use in dependent individuals. It is herein disclosed that Panx1 activation in spinal microglia critically underlies the cellular and behavioral corollary of morphine withdrawal. It is herein disclosed that Panx1 activation is a fundamental mechanism by which microglia unmask long-term synaptic facilitation in spinal LI/II neurons during naloxone-induced withdrawal. It is herein disclosed that ATP is released from Panx1 as a key microglia-to-neuron substrate required for morphine withdrawal. Although ATP in the spinal dorsal horn can derive from various sources, including primary sensory terminals, neurons, or astrocytes, our results indicate that microglia are the critical ATP source for morphine withdrawal. Of particular importance for therapeutic development, it is herein disclosed that blocking Panx1 effectively alleviates morphine withdrawal without affecting analgesia. Thus, targeting Panx1 channels provides a clinical strategy for alleviating the symptoms of withdrawal without affecting morphine analgesia.

The invention claimed is:

1. A method of treating or ameliorating a plurality of symptoms of opioid withdrawal syndrome in a subject, comprising administering to the subject an effective amount of probenecid.

2. The method according to claim 1, wherein the administration is topical administration.

3. The method according to claim 1, wherein the administration is with a transdermal patch.

4. The method according to claim 1, wherein the administration is by an oral dosage.

5. The method according to claim 1, wherein the administration is by an injection.

6. The method according to claim 5, wherein the administration is by a subcutaneous injection.

7. The method according to claim 1, wherein the composition is a topical composition.

8. The method according to claim 7, wherein the composition is in the form of a lotion, a cream, a gel, or a viscous liquid.

9. The method according to claim 8, wherein the composition further comprises one or more of a skin penetration enhancer, an emollient, an emulsifying agent, a water miscible solvent, an alcohol, and mixtures thereof.

10. The method according to claim 9, wherein the skin penetration enhancer is a non-cationic skin penetration enhancer.

11. The method according to claim 1, wherein the subject is human.

* * * * *